United States Patent [19]
Rohrberg

[11] Patent Number: 5,894,844
[45] Date of Patent: *Apr. 20, 1999

[54] THREE-DIMENSIONAL FLOATATION-ENHANCED BODY EXAMINATION SYSTEM

[76] Inventor: Roderick G. Rohrberg, 2742 W. 234th St., Torrance, Calif. 90505

[*] Notice: This patent is subject to a terminal disclaimer.

[21] Appl. No.: 08/743,762

[22] Filed: Nov. 7, 1996

[51] Int. Cl.$^6$ .................................................. A61B 19/00
[52] U.S. Cl. ........................................ 128/898; 600/300
[58] Field of Search ................................. 600/437, 448, 600/549, 300, 445, 443; 128/898

[56] References Cited

U.S. PATENT DOCUMENTS

| | | |
|---|---|---|
| 3,578,971 | 5/1971 | Lasky . |
| 3,603,303 | 9/1971 | Stouffer ........................... 600/437 |
| 3,778,614 | 12/1973 | Hounsfield . |
| 3,806,109 | 4/1974 | Weber et al. . |
| 3,867,634 | 2/1975 | Hounsfield . |
| 3,881,110 | 4/1975 | Hounsfield et al. . |
| 3,963,933 | 6/1976 | Henkes, Jr. . |
| 3,973,126 | 8/1976 | Redington et al. . |
| 4,075,883 | 2/1978 | Glover . |
| 4,130,112 | 12/1978 | Frazer . |
| 4,135,497 | 1/1979 | Meyers et al. ........................... 600/549 |
| 4,206,763 | 6/1980 | Pederson . |
| 4,252,125 | 2/1981 | Iinuma . |
| 4,282,880 | 8/1981 | Gardineer et al. ........................... 600/437 |
| 4,303,861 | 12/1981 | Ekstrom . |
| 4,338,948 | 7/1982 | Perez-Mendez et al. ........................... 600/437 |
| 4,341,222 | 7/1982 | Gardineer et al. ........................... 600/437 |
| 4,347,850 | 9/1982 | Kelly-Fry et al. . |
| 4,478,083 | 10/1984 | Hassler et al. ........................... 600/445 |
| 4,485,819 | 12/1984 | Igl ........................... 600/445 |
| 4,509,368 | 4/1985 | Whiting et al. ........................... 600/448 X |
| 4,541,436 | 9/1985 | Hassler et al. ........................... 600/448 |
| 4,545,385 | 10/1985 | Pirschel ........................... 600/445 |
| 4,616,656 | 10/1986 | Nicholson et al. ........................... 600/300 |
| 4,649,275 | 3/1987 | Nelson et al. . |
| 4,657,021 | 4/1987 | Perry et al. . |
| 4,681,436 | 7/1987 | Ching et al. . |
| 4,737,109 | 4/1988 | Abramson . |
| 4,767,028 | 8/1988 | Rohlfing et al. . |
| 4,772,118 | 9/1988 | Liu et al. . |
| 4,793,354 | 12/1988 | Wright et al. ........................... 600/300 |
| 4,810,875 | 3/1989 | Wyatt . |
| 4,819,752 | 4/1989 | Zelin . |
| 4,867,686 | 9/1989 | Goldstein . |
| 4,873,982 | 10/1989 | Morrison ........................... 600/300 |
| 4,905,700 | 3/1990 | Wokalek et al. . |
| 4,910,404 | 3/1990 | Cho et al. . |
| 4,917,096 | 4/1990 | Englehart et al. . |
| 4,945,239 | 7/1990 | Wist et al. . |
| 5,207,582 | 5/1993 | Michelson . |

(List continued on next page.)

FOREIGN PATENT DOCUMENTS 2111347 11/1982 Germany .

OTHER PUBLICATIONS

"S-ray" brochure published by Mettix Inc., no date.
"Dr. Susan Love's Breast Book", by Susan M. Love, M.D. with Karen Lindsey, 2nd Edition, pp. 21–31.

Primary Examiner—Mickey Yu
Assistant Examiner—Kelly O'Hara
Attorney, Agent, or Firm—Anglin & Giaccherini

[57] ABSTRACT

An examination of a portion of the body, such as a female breast, is conducted in the relaxing environment of floatation. When submerged, the buoyancy of the breast tissue counteracts the effects of gravity, and enhances the examiner's ability to detect abnormalities. While the breast is immersed in warm water, a constricted portion of the breast tissue is examined with the fingers. Forming this constricted three-dimensional projection of tissue is quite different from the generally flat or planar, circular rubbing motions advocated by more conventional methods of breast examination. Although the method is especially useful for conducting a self-examination of the female breast, tissues of the male abdomen and testicles may also be examined using the present invention.

21 Claims, 47 Drawing Sheets

U.S. PATENT DOCUMENTS

| | | |
|---|---|---|
| 5,261,410 | 11/1993 | Alfano et al. . |
| 5,289,520 | 2/1994 | Pellegrino et al. . |
| 5,353,799 | 10/1994 | Chance . |
| 5,371,368 | 12/1994 | Alfano et al. . |
| 5,376,796 | 12/1994 | Chan et al. . |
| 5,385,143 | 1/1995 | Aoyagi . |
| 5,386,447 | 1/1995 | Siczek . |
| 5,386,827 | 2/1995 | Chance et al. . |
| 5,409,497 | 4/1995 | Siczek et al. . |
| 5,415,169 | 5/1995 | Siczek et al. . |
| 5,426,685 | 6/1995 | Pellegrino et al. . |
| 5,432,703 | 7/1995 | Clynch et al. . |
| 5,451,785 | 9/1995 | Faris . |
| 5,474,064 | 12/1995 | Rohrberg ................................ 600/300 |
| 5,477,051 | 12/1995 | Tsuchiya . |
| 5,477,371 | 12/1995 | Shafir . |
| 5,479,661 | 1/1996 | Fingleson et al. . |
| 5,530,579 | 6/1996 | Nakamura et al. . |
| 5,555,885 | 9/1996 | Chance . |
| 5,572,995 | 11/1996 | Rohrberg ................................ 600/300 |
| 5,609,152 | 3/1997 | Pellegrino et al. . |
| 5,692,511 | 12/1997 | Grable . |

THREE-DIMENSIONAL FLOATATION-ENHANCED BODY EXAMINATION SYSTEM

CROSS-REFERENCE TO RELATED PATENT & A RELATED PATENT APPLICATION

The present Patent Application is related to commonly-owned U.S. Letters Pat. No. 5,474,064 entitled *Breast Self-Examination Floatation System* by Roderick G. Rohrberg, which was granted on Dec. 12, 1995. The present Patent Application is also related to a commonly-owned and allowed U.S. Patent Application entitled *Floatation Enhanced Self-Examination System*, which was filed on Jun. 1, 1995 and which was issued U.S. Ser. No. 08/456,438.

FIELD OF THE INVENTION

The present invention pertains to a three-dimensional examination or self-examination of various parts of the human body. More particularly, the present invention utilizes novel finger tip examination methods in a relaxing floatation environment which levitates portions of the body to enhance awareness of the body's condition. The combination of the floatation effect and the relaxing environment created by a hot bath permit the internal structure of the examined tissue to shift position readily and painlessly permitting greater access to any abnormality that could potentially be obscured by normal internal breast structure. Present two-dimensional procedures are unable to offer the enhanced detection capabilities offered by the novel Perfect Way Finger Walk$^{SM}$ methods described below.

BACKGROUND OF THE INVENTION

According to a recent study by the American Cancer Society, 46,000 women in the United States will die in 1993 from breast cancer. (From the 1993 *World Almanac*, published by Pharos Books.) Recent advances in diagnostic techniques and surgical treatments have helped to reduce the mortality rate due to breast cancer, but this disease is still the third greatest cause of death among women in this country. A variety of mammographic systems which employ X-rays and ultrasound have been developed over the past few decades, but this equipment is generally very large, prohibitively expensive and requires a trained technician to operate them. As an example, the minimum price of an ultrasonic imaging system sold by Acuson of Mountain View, Calif. exceeds $200,000. Several documents noted below disclose various systems that pertain to equipment that may be used for different kinds of medical diagnosis.

In U.S. Pat. No. 4,282,880, Gardineer et al. disclose a water conditioning system for maintaining and conditioning the water used in an ultrasound imaging system especially adapted to perform diagnosis of the human breast.

In his U.S. Pat. No. 4,737,109, Abramson discloses a method and apparatus for use in training persons in breast cancer detection by manual examination. The apparatus includes a device which is comprised of a body of elastomerically yielding material and one or more lumps embedded in the body, wherein the lump or lumps resemble a pre-determined type of lesion.

In their U.S. Pat. No. 4,793,354, Wright and Perry disclose a method of enhancing the sense of touch.

In his U.S. Pat. No. 4,867,686, Goldstein uses a model of a human female breast for teaching breast examination. Goldstein discloses a method of training a person to detect breast tumors by palpating a model of a human female breast having at least one simulated tumor.

In his U.S. Pat. No. 5,207,582, Michelson discusses a device for facilitating breast self-examination in order to speed up detection of breast cancer. The device has an information panel, instructions for conducting self-examinations and diagrams for recording the results. Recording means are also included with this device.

In their U.S. Pat. No. 5,479,661, Fingleson and Richman teach the use of a garment worn by a woman for self-examination of the breasts, the device having written and graphic instructions printed on it.

In his U.S. Pat. No. 4,130,112, Frazer describes an apparatus for ultrasonic scanning of a breast or other tissue. This invention includes a cavity for receiving the patient's breast, and a vacuum for drawing the breast into intimate contact with the walls of the cavity. The walls enclose ultrasonic transducers that are employed to create an image of the breast tissue.

U.S. Pat. No. 4,135,497 issued to Meyers et al. reveals an apparatus for detecting temperature variations over selected regions of living tissue. The inventors state that the method disclosed in their patent is useful for detecting malignant tissue in the breasts.

U.S. Pat. No. 4,206,763 issued to Pedersen discloses a device and a method for ultrasonic examination for carcinoma of the breast. Pedersen employs a compartment in which water is drawn upward by suction over the breast. An ultrasonic transducer then revolves around the breast to obtain complete 360 degree scans. A pleated flexible bag 12 pulls the breast into a water bath compartment 4 when the water bath compartment 4 is evacuated by a pair of bellows 16. (See Column 1, Lines 60–68; Column 3, Lines 23–51 and Column 4, Lines 4 & 5.)

U.S. Pat. No. 4,252,125 issued to Iinuma describes an ultrasonic diagnosing apparatus that utilizes a receptacle 11 filled with warm water 12. An ultrasonic probe 14 makes an image of the breasts, which are pressed against a flexible membrane 18 that is stretched in front of the probe. (See Column 1, Lines 65–68 and Column 2, Lines 1–7.)

U.S. Pat. No. 4,341,222 issued to Gardineer et al. relates to a patient support system for orienting a woman's breast over an ultrasound scanner. The patient is shown bent over a pool of water 20 that is positioned over a scanning transducer 14. (See Column 5, Lines 62–68 and Column 6, Lines 1–4.) The water serves as a transmission medium for the ultrasonic waves. (See Column 2, Lines 15 & 16.)

U.S. Pat. No. 4,347,850 issued to Kelly-Fry et al. discloses a direct water coupling device for ultrasound scanning. A tank 10 is placed in a sealed position about the perimeter of the breast area while the patient is in a supine position. (See FIG. 3 & Column 4, Lines 37–38.)

U.S. Pat. No. 4,545,385 issued to Pirschel describes an apparatus for ultrasonic examination of body parts using a fluid container and an ultrasound scanning system. (See FIG. 1.) A liquid-filled basin 6 serves as an acoustic coupling. (See Column 3, Lines 4–5 & Column 3, Lines 24–25.) U.S. Pat. No. 4,657,021 issued to Perry et al. concerns an apparatus which he claims enhances the sense of touch when placed between the fingertips of the user and the object being touched. A liquid lubricant 13 is captured inside a sealed enclosure 10 made from a pliable, elastic material. (See Column 2, Lines 36–40 and Column 3, Lines 4–18.)

U.S. Pat. No. 4,873,982 issued to Morrison contains a discussion of an examination garment that may be used to feel for lumps under the skin. (See FIGS. 1 and 3.)

U.S. Pat. No. 4,917,096 issued to Englehart et al. reveals the details of a portable ultrasonic probe. A fluid-filled enclosure is coupled to a handled portion which houses a drive motor. (See FIG. 3.) The probe 20 includes a fluid-filled enclosure 34. (See Column 4, Lines 30–31.)

U.K. Patent Application No. 2,111,347A by Robert Cribbs pertains to a method of pulse examination using a container that holds a liquid couplant. The container is placed about the breasts of a female torso, and breast tissue is scanned using ultrasound.

A brochure published by Metrix Incorporated of Deerfield, Ill. presents specifications for echo-scan and echo-trace ultrasonic analyzers. The brochure describes how high frequency, short duration electromechanical pulses emitted by special transducers in direct or indirect contact with a portion of the human body can produce visual information.

In her book entitled *Dr. Susan Love's Breast Book*, Susan M. Love describes conventional techniques for breast self-examinations. (See pp. 21–31).

The vast majority of literature published in both the academic and popular press suggests that the best weapon in the fight against breast cancer is early detection. The problem of providing a low-cost yet effective method for self-examination of portions of the human body has presented a major challenge to doctors and other health-care professionals. The development of methods and apparatus that enhance the prospects of detecting abnormalities during self-examinations would constitute a major technological advance and would satisfy a long felt need within the health-care field.

SUMMARY OF THE INVENTION

The *Three-Dimensional Floatation-Enhanced Body Examination System* comprises apparatus and methods for performing a three-dimensional finger tip examination of portions of the human body utilizing the beneficial effects of floatation. The method is especially useful for conducting an examination of the female breast. In the preferred embodiment of the invention, a patient relaxes in a tub filled with hot water. The physical relaxation created by the bath brings about a concomitant state of mental relaxation. When the breast is substantially submerged, the buoyancy of the breast tissue in the water counteracts the effects of gravity. The buoyancy of the water enhances the ability of the patient herself or a second person to probe the breast tissue to detect abnormalities.

By using the Finger Walk$^{SM}$ method of the preferred embodiment, aberrations in the breast may be discovered at an early stage. In the preferred embodiment of the invention, gentle pressure is applied systematically to localized areas using the finger tips. This pressure is applied to the breast tissue in a repetitive, palpating motion.

The floatation effect and the relaxing environment created by a hot water bath endows the examiner with an exceptional ability to detect abnormalities in the patient. The methods described and claimed below permit finger tip penetration of an unusual order of magnitude that are not possible to realize using conventional techniques. The floatation effects blossom the breast into a full and very manageable shape that permits the unique Finger Walk$^{SM}$ method to detect abnormalities that are not generally sensed by conventional techniques.

The combined effects of floatation and relaxation permit the penetration of the finger tips of an unusual order of magnitude that present conventional methods can not accomplish because they are essentially two-dimensional techniques performed while the patient is in a supine position under the full effects of gravity. Internal breast structure may "pile up" under normal gravitational forces, masking the presence of abnormalities and reducing the effectiveness of an exam. The floatation forces blossom the breast into a full and very manageable shape that permits the unique Finger Walk$^{SM}$ method to detect abnormalities heretofore unknown to industry.

The present invention stimulates the flow of the lymph fluid in the lymphatic system and stimulates the blood flow through the capillary blood vessels in the breast. The Finger Walk$^{SM}$ technique may break up lumpy clusters in the lobules which would appear to entrap and restrain proper lymphatic and blood flow in the breast tissues. The stimulation and subsequent freeing of these clusters may diminish lumpiness in the breast tissue.

The Perfect Way Finger Walk$^{SM}$ methods are radically different from those employed in conventional breast exams and mammographic techniques. The present invention provides methods which are relaxing and painless. The Perfect Way promotes self-awareness of the body and supplies an easy method that can be employed on a regular and frequent basis.

An appreciation of other aims and objectives of the present invention and a more complete and comprehensive understanding of this invention may be achieved by studying the following description of preferred embodiment and alternative embodiments and by referring to the accompanying drawings.

BRIEF DESCRIPTION OF THE DRAWINGS

In FIG. 6, the patient is shown in a lateral view in an upright position and the examiner is checking tissue near the rib cage.

FIGS. 32 and 33 show the Finger Walk$^{SM}$ "S" Curve.

Figure 48:
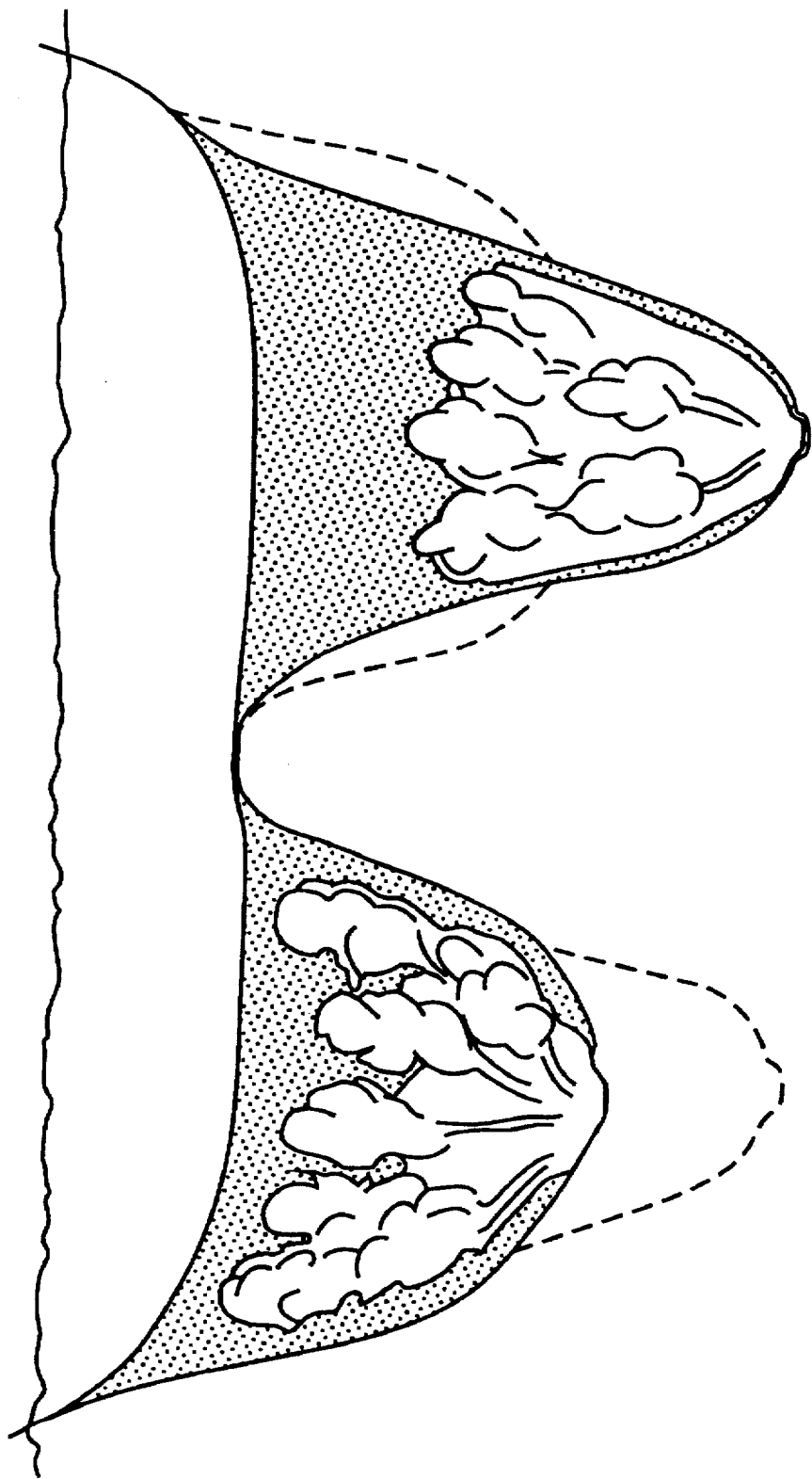

The right side of FIG. 48 reveals the migration of fatty tissue when a patient in a prone position immerses her breasts in water. The right side of FIG. 49 portrays the emulsification of fatty tissue within the breast when the patient is in the prone position. In this position, the internal structure can free itself and tends to migrate toward the nipple. The left side of FIG. 49 portrays the emulsification of fatty tissue immediately upon removal from the water bath.

Figure 50:
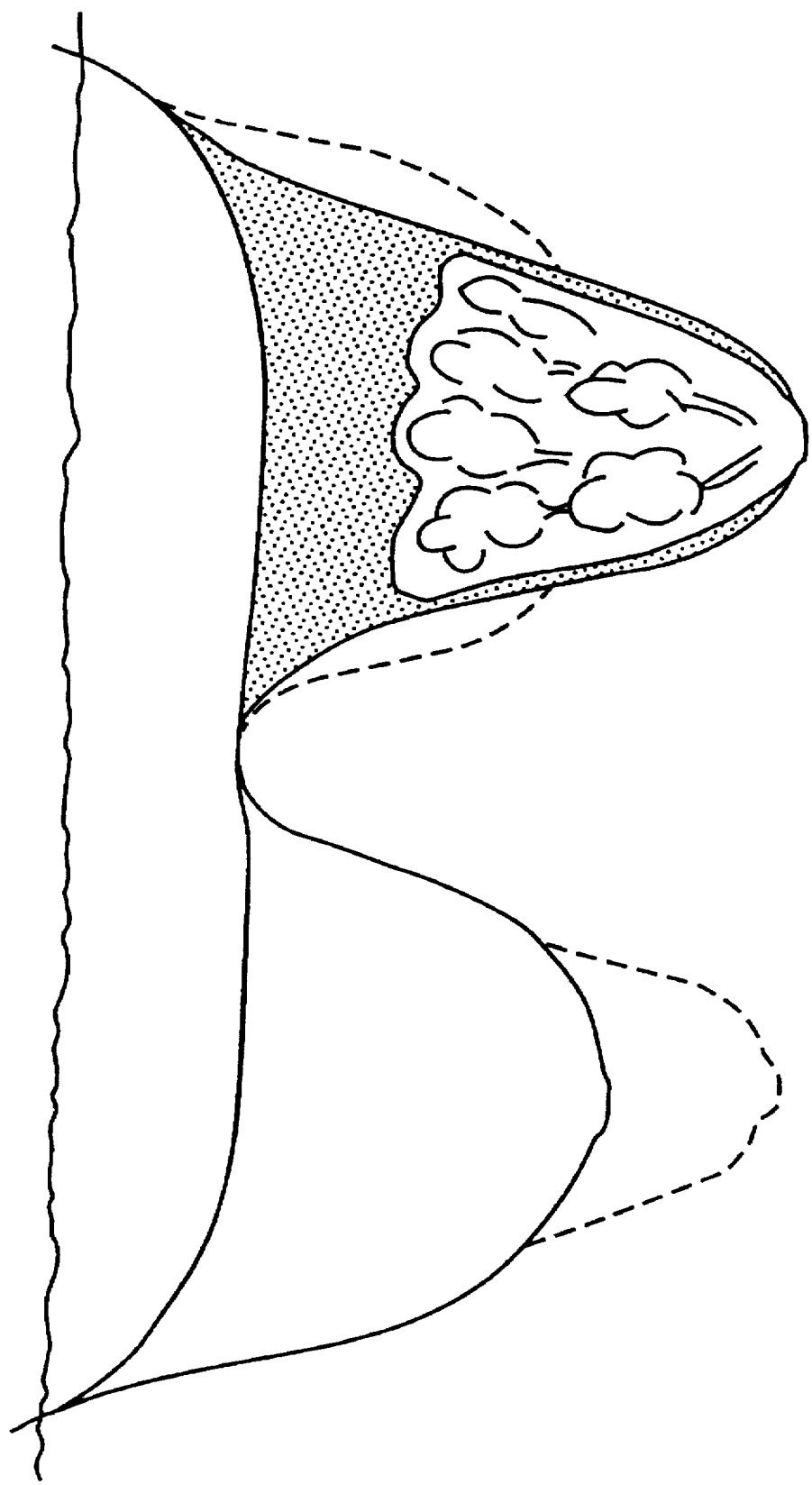

FIG. 50 illustrates the condition of the fatty tissue after submersion in a hot bath followed by cooling to room temperature.

Figure 51:
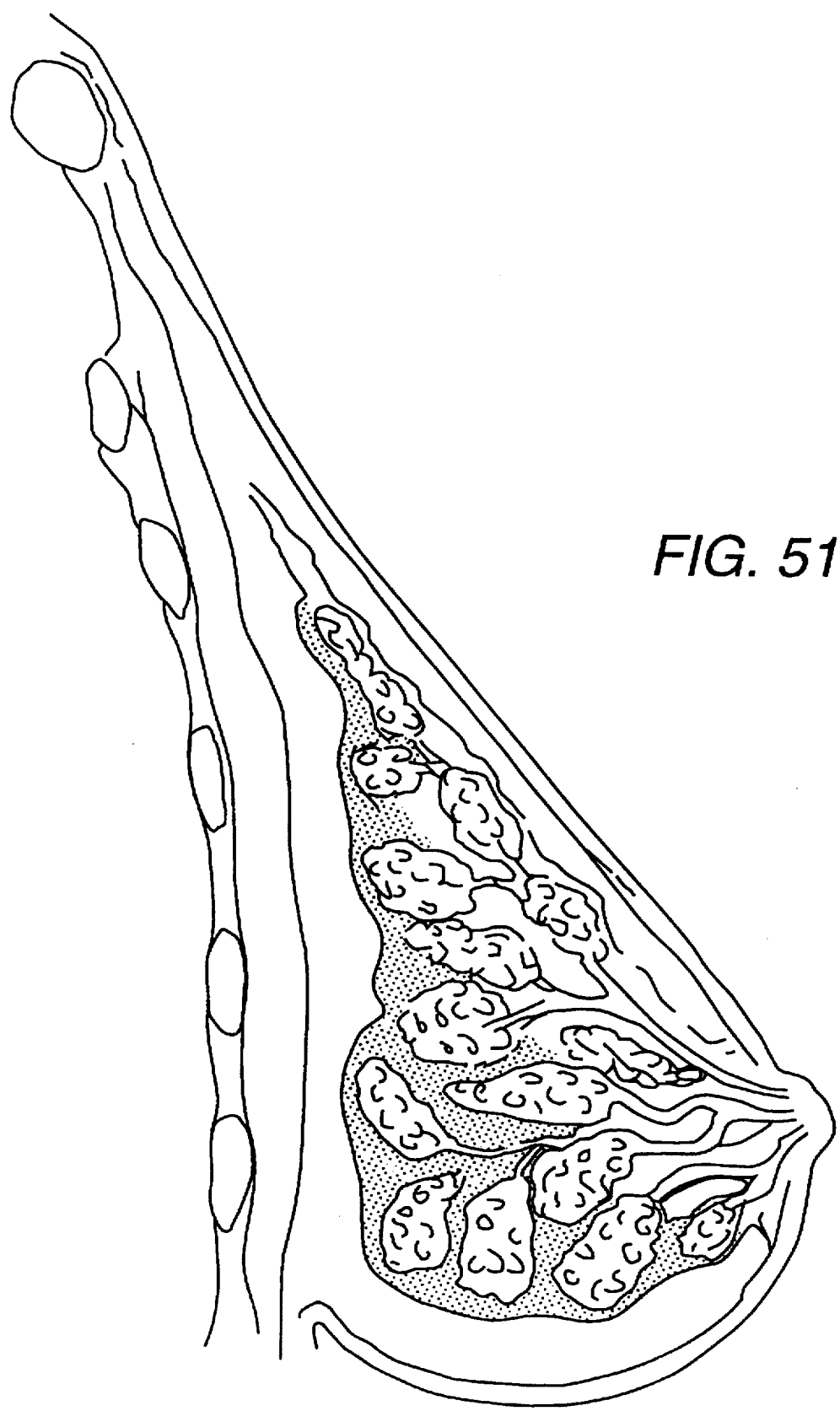
Figure 52:
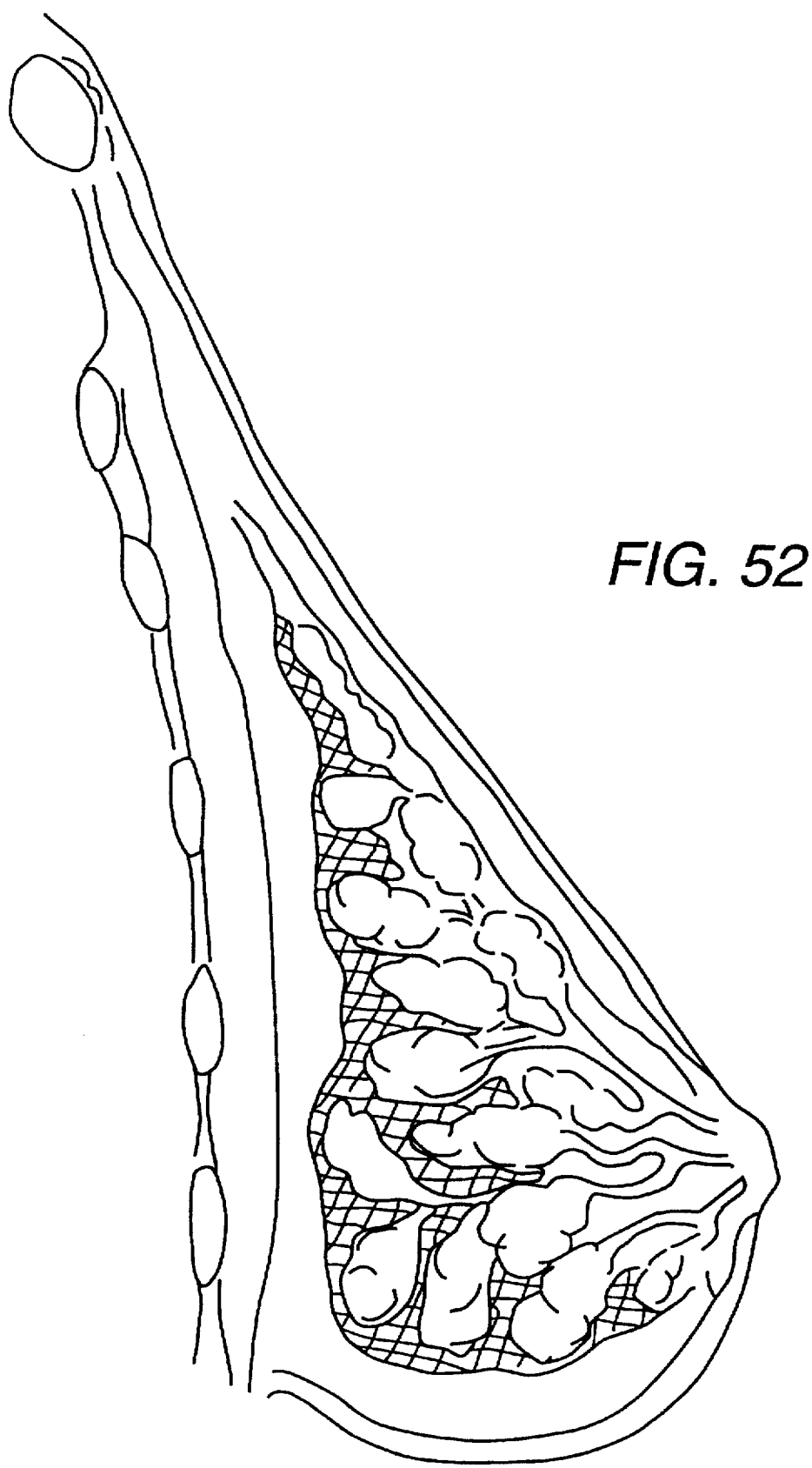
Figure 53:
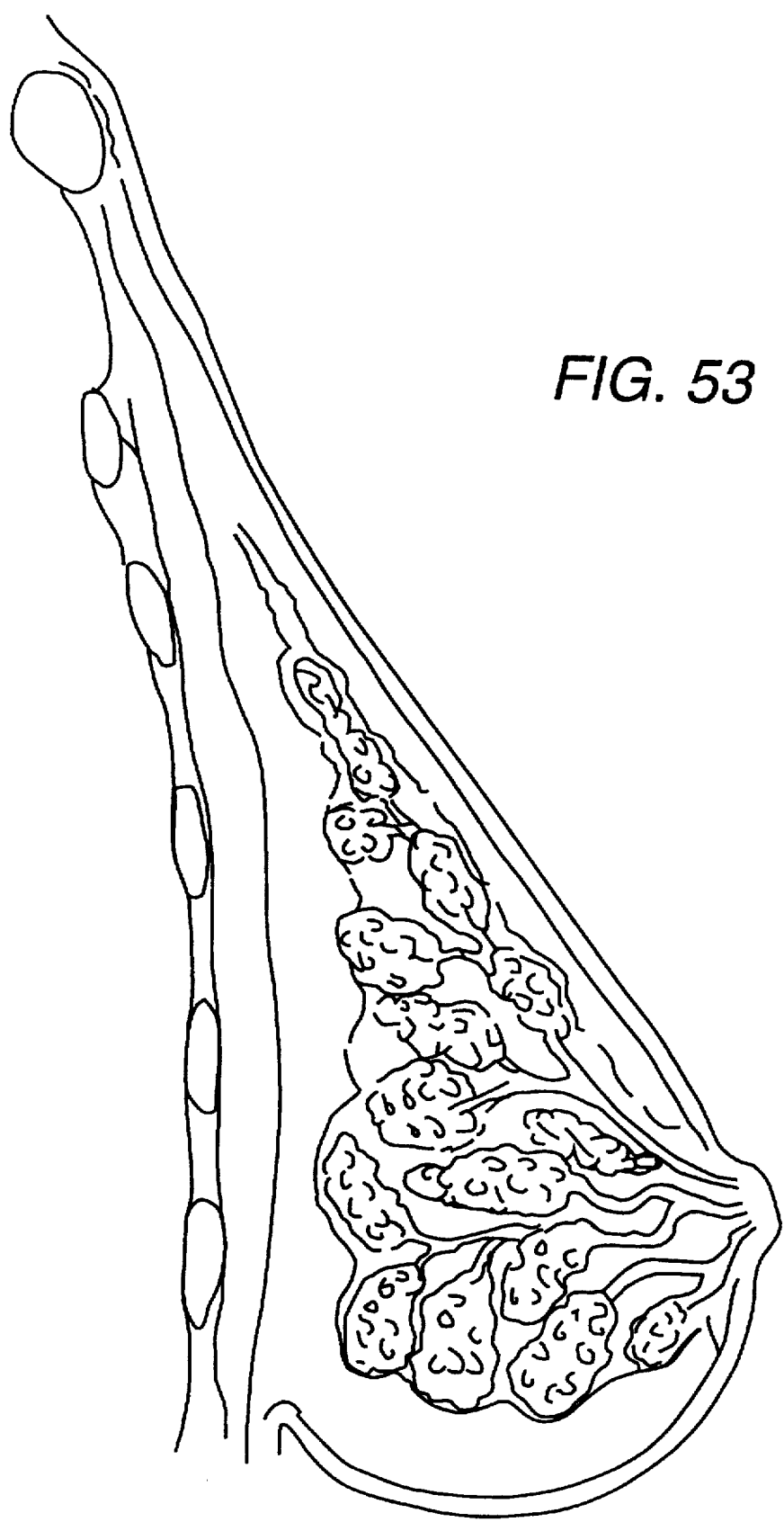

FIG. 51 shows a breast in cross-section while the patient is in an upright position, and reveals the migration of fatty tissue. FIGS. 52 and 53 provide the same view as FIG. 51, but after a hot bath and massage.

Figure 54:
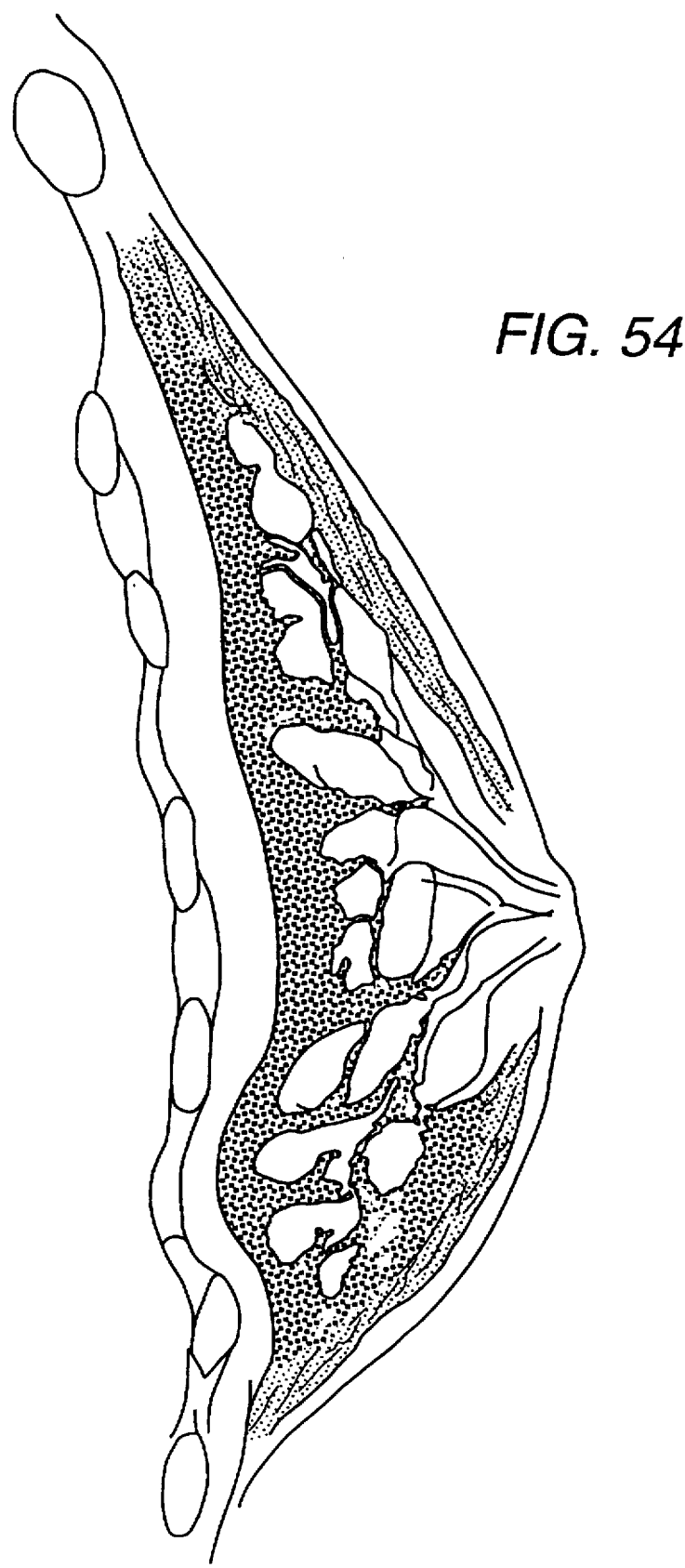
Figure 55:
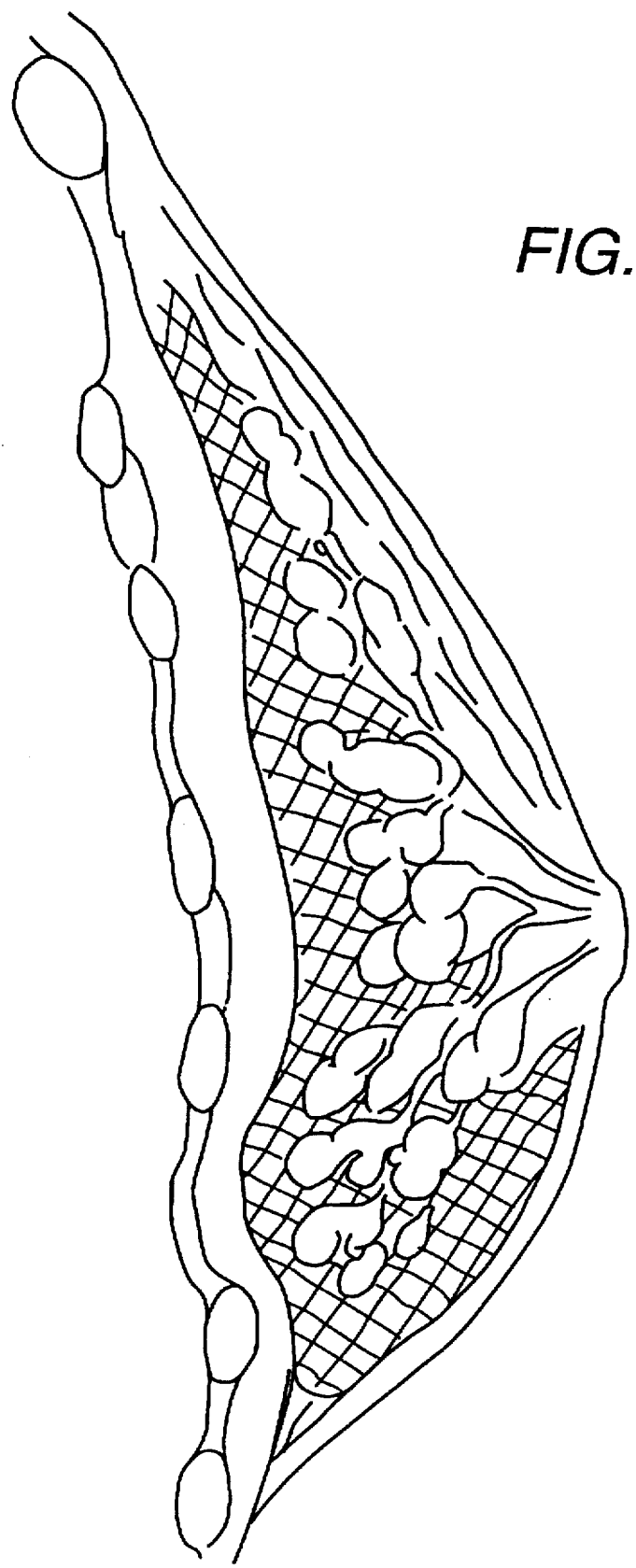
Figure 56:
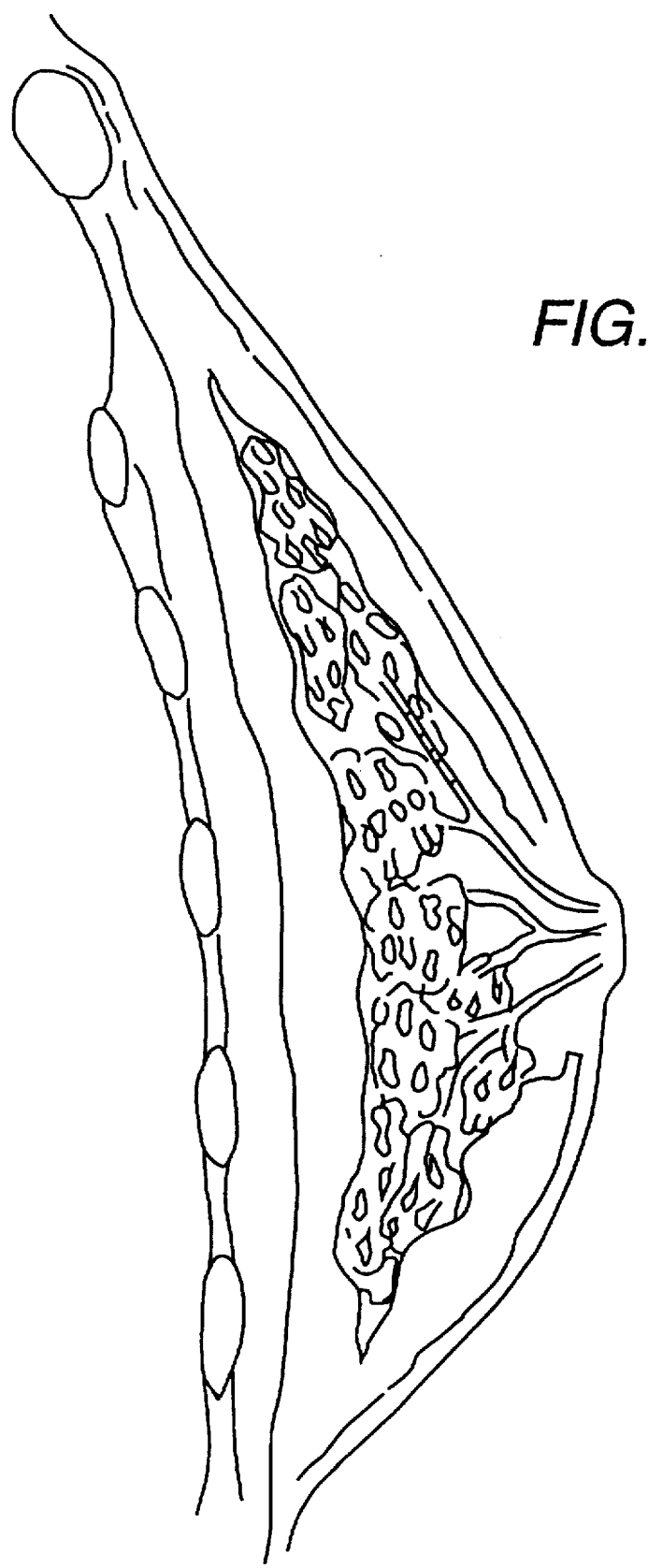

FIG. 54 shows the fatty tissue migration into the internal structure of the breast when the patient is in a supine position. FIG. 55 shows the same breast after the emulsification that occurs during a hot bath and massage, while FIG. 56 illustrates the same tissue after it is cooled to normal body temperature.

FIGS. 57 through 64 are computer-generated representations of breasts under floatation. These figures present digitized representations of the surfaces of a mold of a patients' breasts made under the influence of floatation.

DETAILED DESCRIPTION OF PREFERRED & ALTERNATIVE EMBODIMENTS

The Basic Finger Walk$^{SM}$ Method

Figure 1:
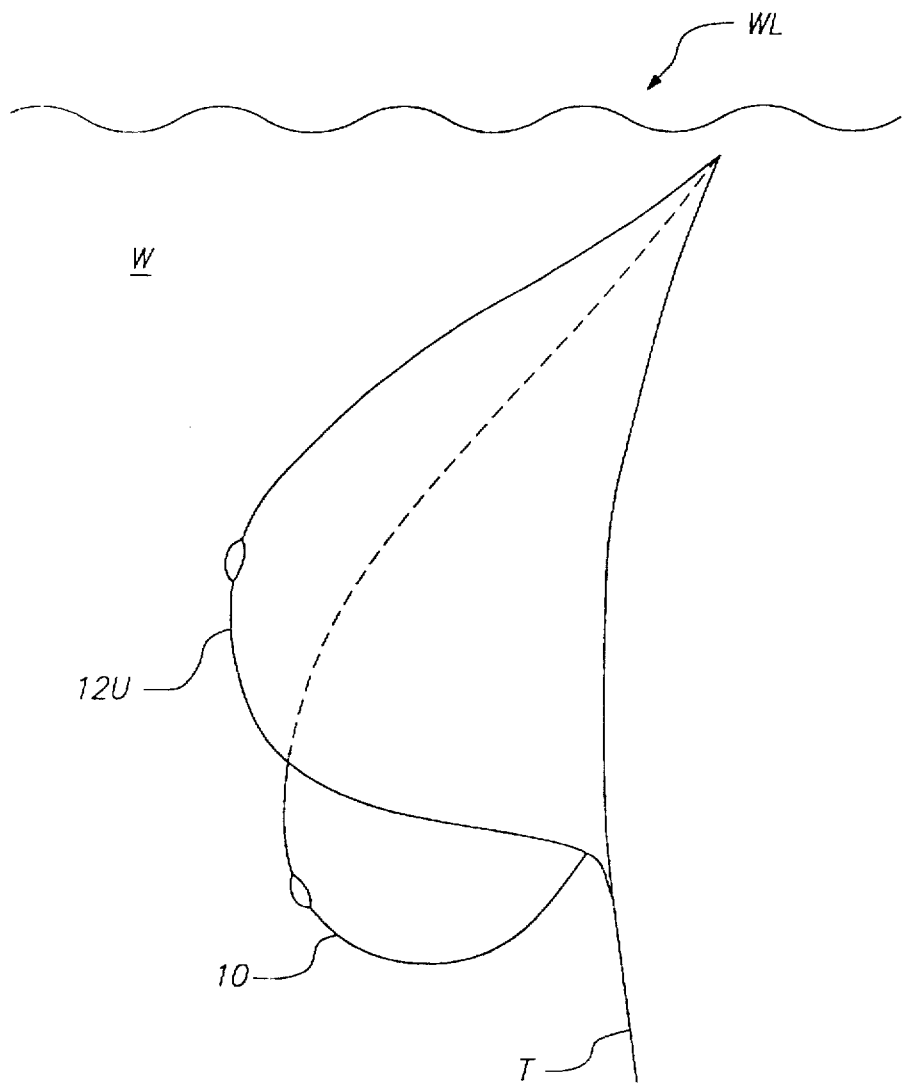
FIG. 1 is a cross-sectional view which compares a female breast in a pendent position and in the levitated position which occurs when it is immersed in water.

FIG. 1 furnishes cross-sectional, superimposed views of a single female breast. In this figure, the patient is positioned in an upright posture, leaning forward at an angle of approximately five to fifteen degrees. In one view, the breast is shown extending from the torso T in its normal, unsupported and pendent position 10. The second view shows the position of the same breast when the breast is immersed in water W. This immersion is accomplished by having the patient sit in a tub filled with hot water. This second position, indicated by the reference character 12U, is the natural or undeflected position of the breast under the influence of the levitating effects of the water W. When the breast is substantially submerged below the water line WL, the buoyancy of the breast tissue in the water counteracts the effects of gravity. Although other fluids such as salt-water may be employed to exaggerate the differences in density between the breast and the fluid medium, and to further lift the breast tissue, ordinary hot water is utilized in the preferred embodiment of the invention. According to the preferred embodiment of the invention, the best temperature range for the hot water is 101 to 104 degrees Fahrenheit.

This buoyancy or "floatation" effect enhances the ability of the patient herself or a second person to test the breast tissue to detect abnormalities. The levitating effects of the present invention allow the internal structure of the breast to float out of the way of the examiner's probing fingertips. By using the Finger Walk$^{SM}$ method of the preferred embodiment, aberrations in the breast may be discovered at an early stage.

Figure 2:
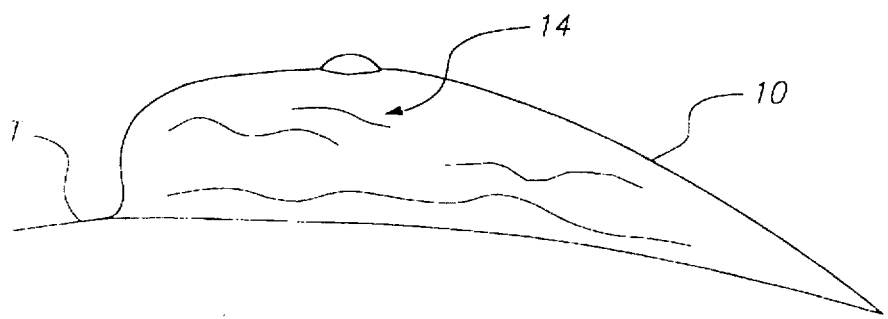
FIG. 2 is a cross-sectional illustrations of a female breast in a supine position in its undeflected non-floatation position.
Figure 3:
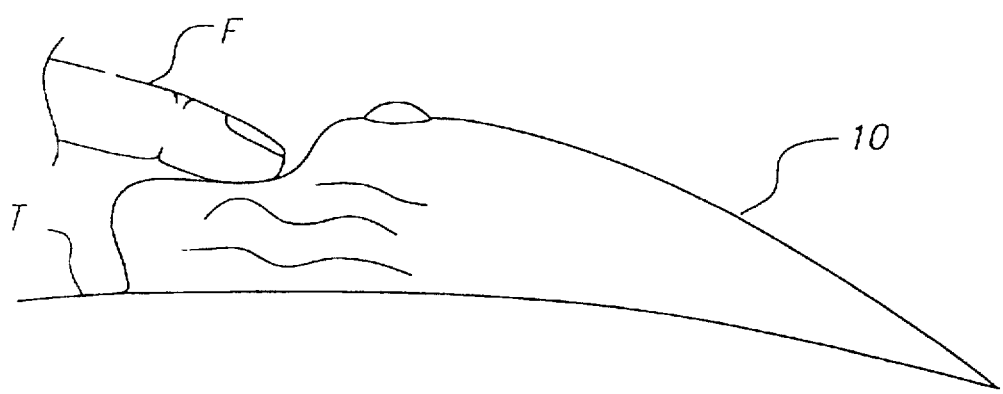
FIG. 3 shows the same breast when deflected by the examiner's fingers.

FIGS. 2 and 3 provide additional cross-sectional illustrations of a female breast which is not immersed in water. In FIG. 2, the patient is reclining on her back in a supine posture. As a consequence, the breast occupies a normal flattened position. The collapsed, overlapping internal structure of the breast is identified by reference character "14". FIG. 3 illustrates the finger F of an examiner who engages or palpates the breast as shown in FIG. 2 to detect abnormalities. This collapsed tissue 14, which may "pile up" in the absence of floatation forces, may cause health problems and may make it difficult for an examiner to detect an abnormality during a conventional examination. The levitation forces of the hot bath may assist the examiner by reducing the entanglement of internal tissues of the breast which, in turn, may increase the chances of detecting an abnormality. The hot bath may also emulsify fatty tissue within the breast, which would also enhance the examiner's ability to detect an abnormality.

In this Specification, the term "examiner" refers to both the patient herself or to a second person who may stroke the tissue in an attempt to detect abnormalities. Although the preferred embodiment of the invention pertains to the examination of the female breast, the present invention may be beneficially employed to examine a variety of body parts of both genders, including tissues of the male abdomen and testicles.

Figure 4:
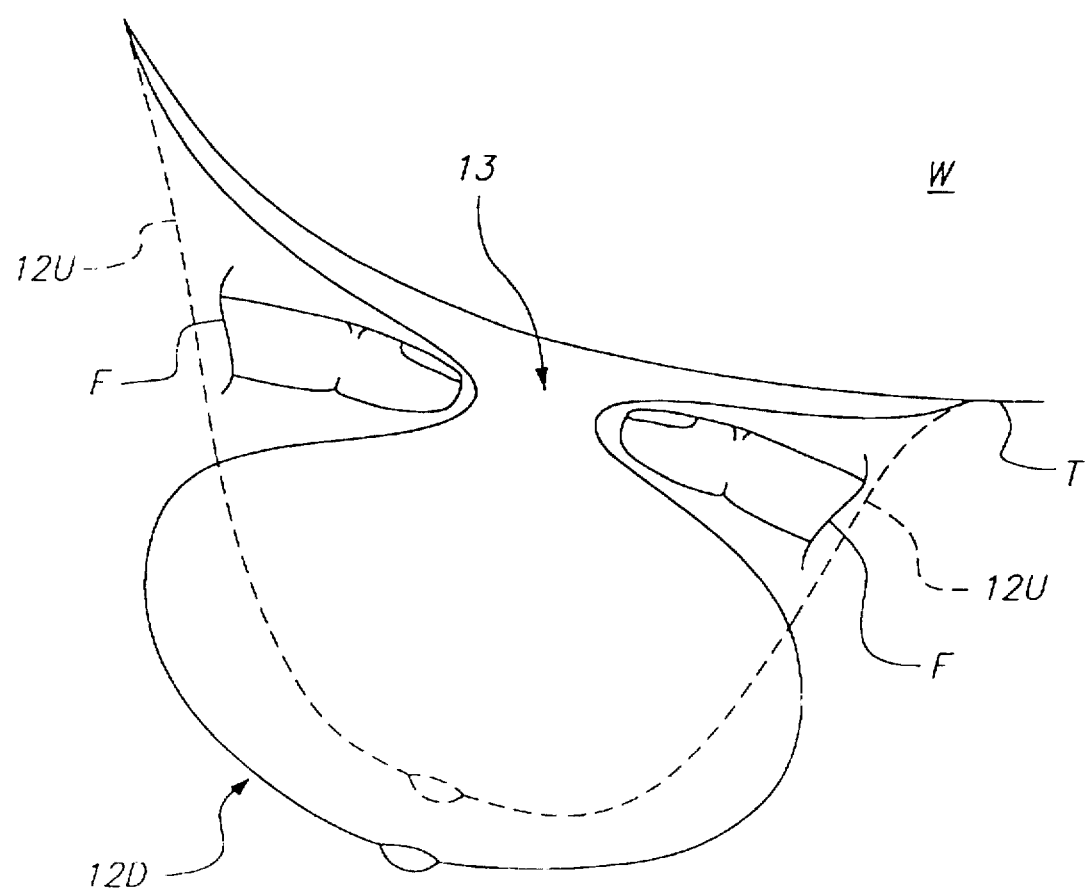
FIGS. 4 and 5 show cross-sectional depictions of a female breast in a top view in floatation in both an undeflected pendent position and in a deflected position that occurs during examination.
Figure 5:
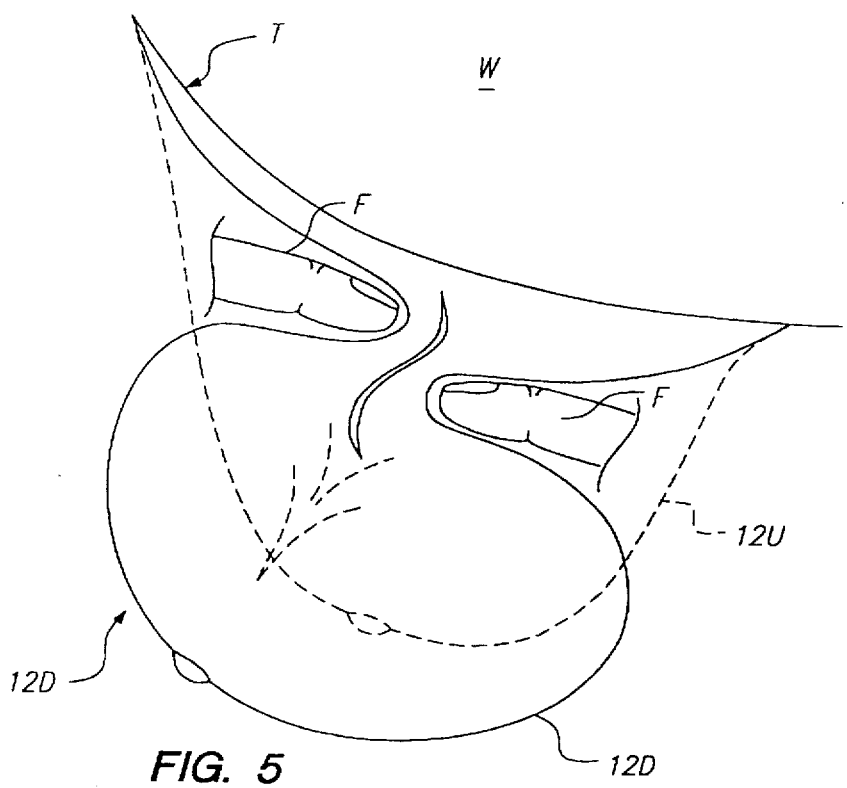

FIGS. 4 and 5 provide two superimposed views of a single breast. The perspective in both cross-sectional views is from the overhead position, looking down into the water bath towards the immersed breast. In both FIGS. 4 and 5, the patient is in an upright position, leaning forward approximately five to fifteen degrees. One depiction, indicated by 12U, represents the breast in a natural undeflected position under the effects of floatation. The second depiction, indicated by 12D, illustrates the shape of the breast after it has been deflected by the gentle probing action of the examiner's finger tips FT. The constricted portion of the breast that lies between the examiner's finger tips FT is indicated by reference character 13. It is this ability to obtain the narrow constriction that greatly enhances the sensitivity of the detection procedure. Without forming the constricted portion of the tissue, the examiner's ability to detect an abnormality may be reduced. Forming this constricted three-dimensional projection is quite different from the generally flat or planar, circular rubbing motions advocated by more conventional methods of breast examination. The enhanced sensitivity offered by the Three Dimensional Perfect Way Finger Walk method is not available to patients who rely on conventional breast-exam and mammographic techniques.

In the preferred embodiment of the invention, slight pressure is applied to the breast tissue simultaneously using the tips of the fingers of both hands. The hands are placed in a position that allows the tips of the fingers of opposite hands to face each other. This arrangement of the fingers is referred to as the "opposing" position of the fingertips. When the tips of the fingers are used to probe the tissue in this opposing position, the capacity to detect abnormalities is enhanced. The heightened sensitivity results from the improved sensory ability of the finger tips to discover an abnormality when it is caught between the two opposed surfaces of the finger tips.

Figure 6:
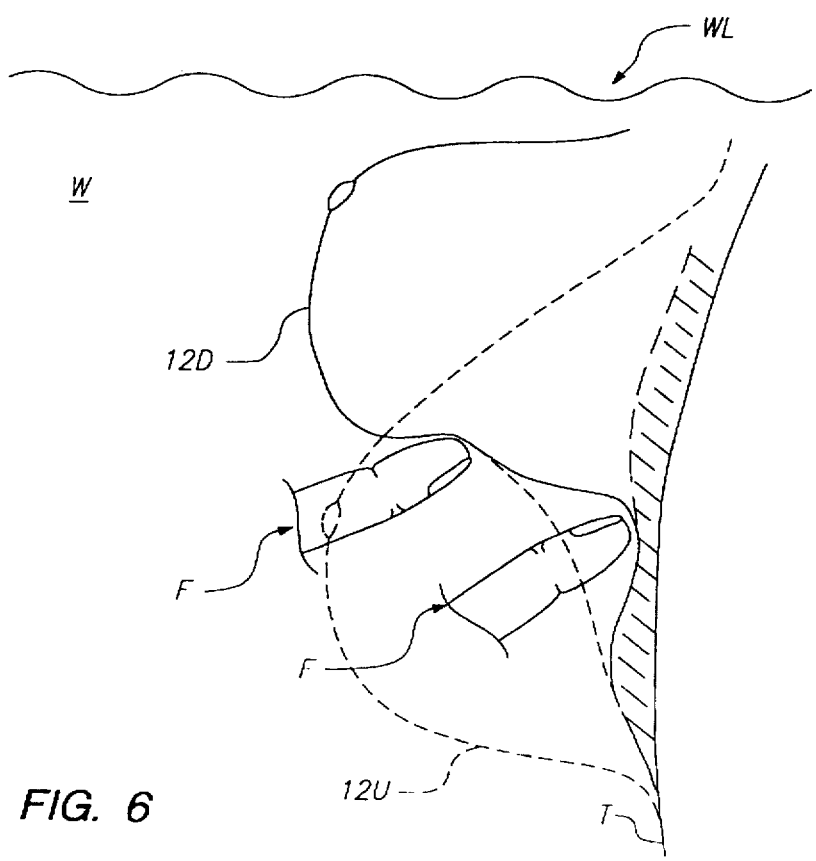
FIG. 6 provides a cross-sectional representation of a female breast in floatation in both undeflected and deflected positions.

Unlike conventional examination methods, the floatation environment allows the breast to assume its full, undistorted and natural position and shape. Conventional breast examination procedures often involve the use of the supine position and other positions which introduce muscle and tissue distortions caused by the placement of the patient's arms over her head. Other tissue distortions are caused by gravity. The present invention eliminates these unwanted effects by counteracting all forces which would tend to block the patient's ability to perform an examination. FIG. 6 presents side views of a female breast under floatation forces. In this view, the patient is in an upright position, leaning forward slightly (approximately five to fifteen degrees). The outline marked "12U" represents the position of the levitated breast without any deflection forces introduced by the examiner. The outline marked "12D" represented the position of the levitated breast after it has been deflected by the examiner. The outline indicated by reference character 12D reveals how the breast can be gently floated out of the way exposing the structure near the rib cage.

Figure 7:
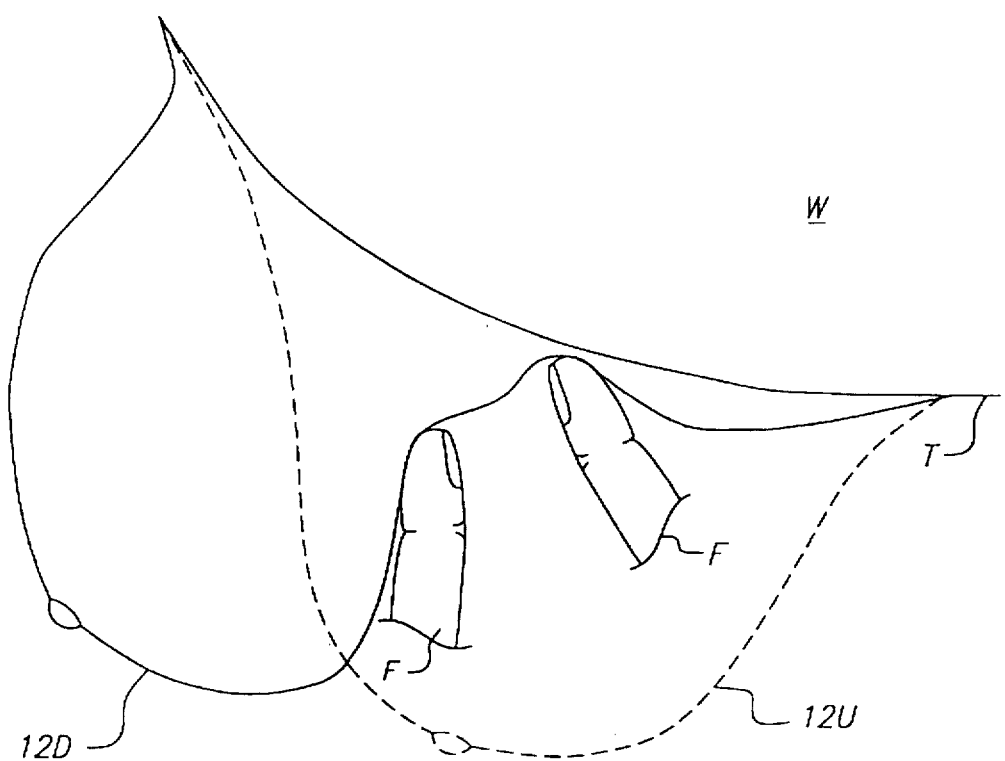
FIGS. 7, 8 and 9 exhibit cross-sectional diagrams of a female breast in floatation in overhead views. Both undeflected and deflected conditions are shown in each drawing.
Figure 8:
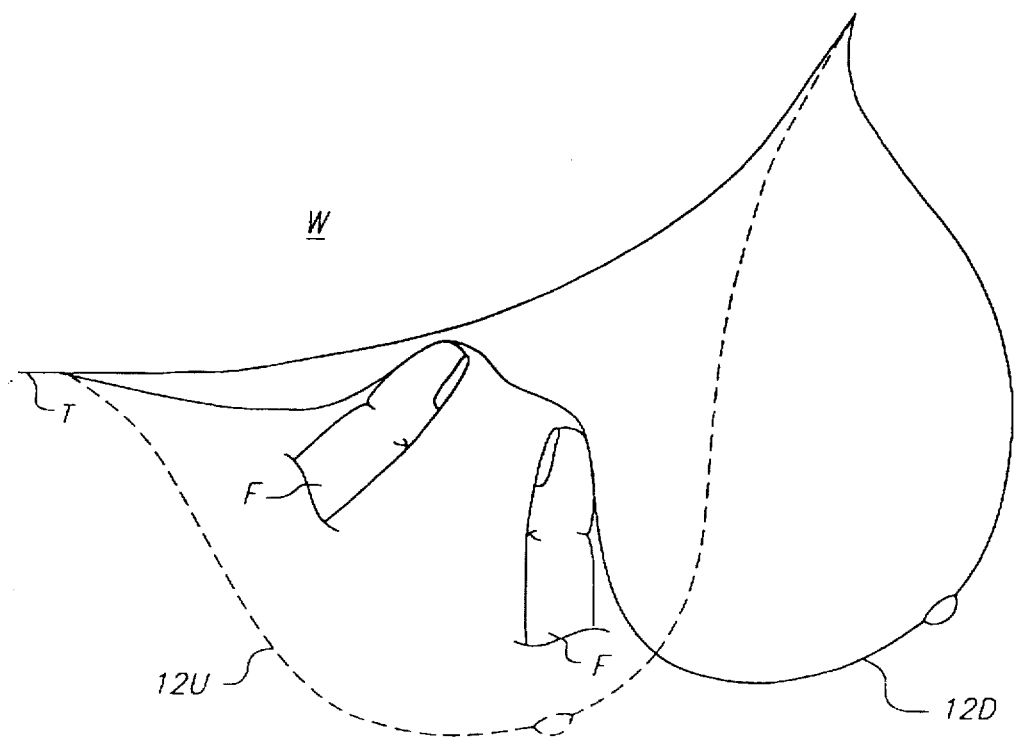
Figure 9:
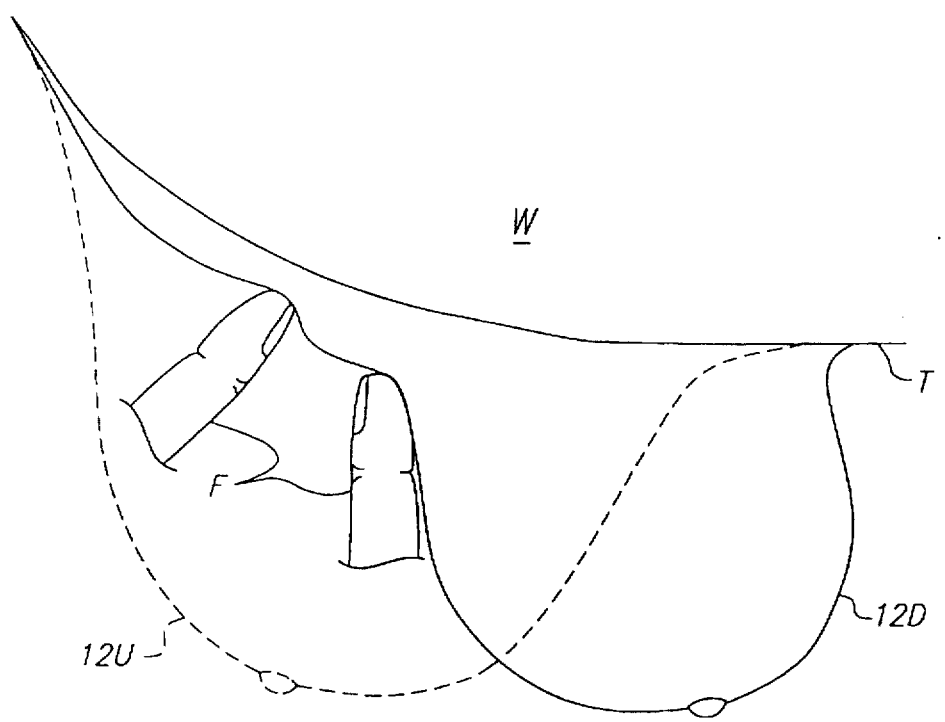

FIGS. 7, 8 and 9 finish three additional overhead views of the patient during an examination. While the patient is sitting with her breasts immersed in an upright position and leaning forward slightly, the examiner uses his or her fingers F to gently probe the breast tissue. In FIG. 7, the examiner probes the patient's right breast (shaded) in the area of the rib cage. FIG. 8 illustrates an examination of the patient's left breast (shaded). FIG. 9 supplies yet another view of an examination of the patient's right breast (shaded).

Figure 10:
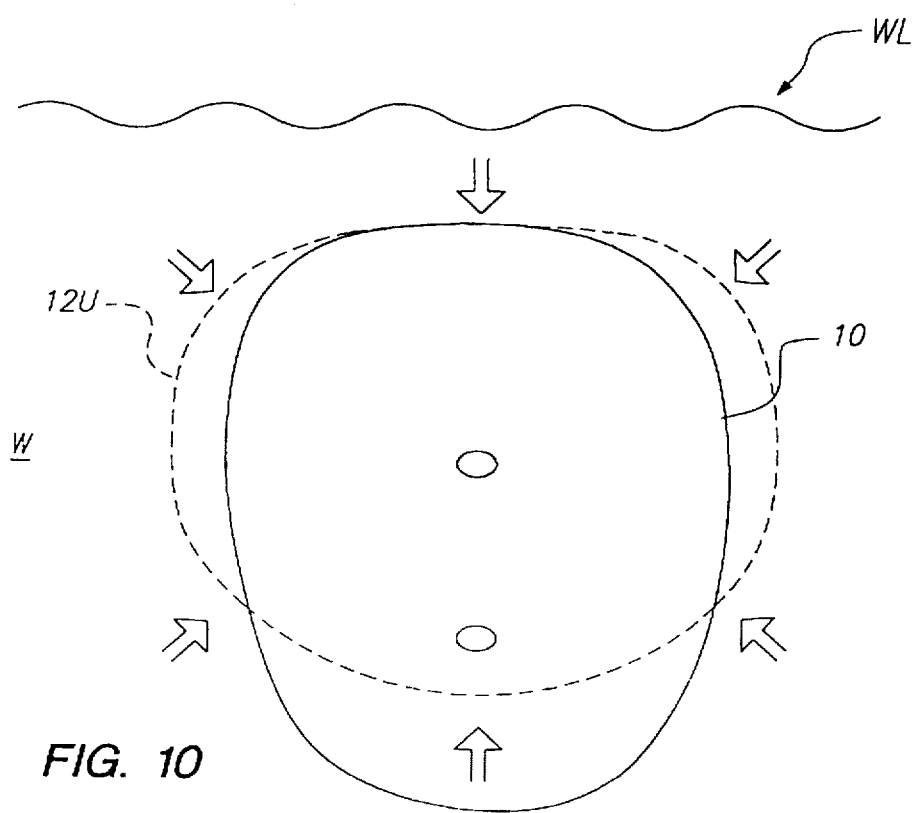
FIG. 10 supplies frontal view of a female breast both under the effects of floatation and under non-floatation conditions. This figure also exhibits the anticipated direction of the opposed fingers in the Finger Walk$^{SM}$ method of examination.

FIG. 10 supplies front view of a female breast, both under the effects of floatation and under non-floatation conditions. The arrows in FIG. 10 represent positions around the circumference of the breast where the examiner may place his or her fingers to begin the Finger Walk$^{SM}$ method. In one embodiment of the invention, the examiner places the fingers from each hand at opposite positions of the generalized "circle" formed by the periphery of the breast where it meets the torso. As a convenient reference, the unmarked arrows in FIG. 10 may be associated with the hour positions of the clock. "Opposite pairs of positions" means twelve and six o'clock, one and seven o'clock and four and ten o'clock et al. The examiner would first perform an examination starting at one of the opposite pairs, and then proceed around the circumference of the breast to perform a complete test for abnormalities as may be necessary.

The floatation influence of the water bath on the breast permits the examiner to gently move the breast tissue to one side so that tissue immediately adjacent to the breast may be tested for abnormalities. By moving the breast to one side, the examiner may also gain access to testing the tissues beneath the breast which are adjacent to the rib cage.

Figure 11:
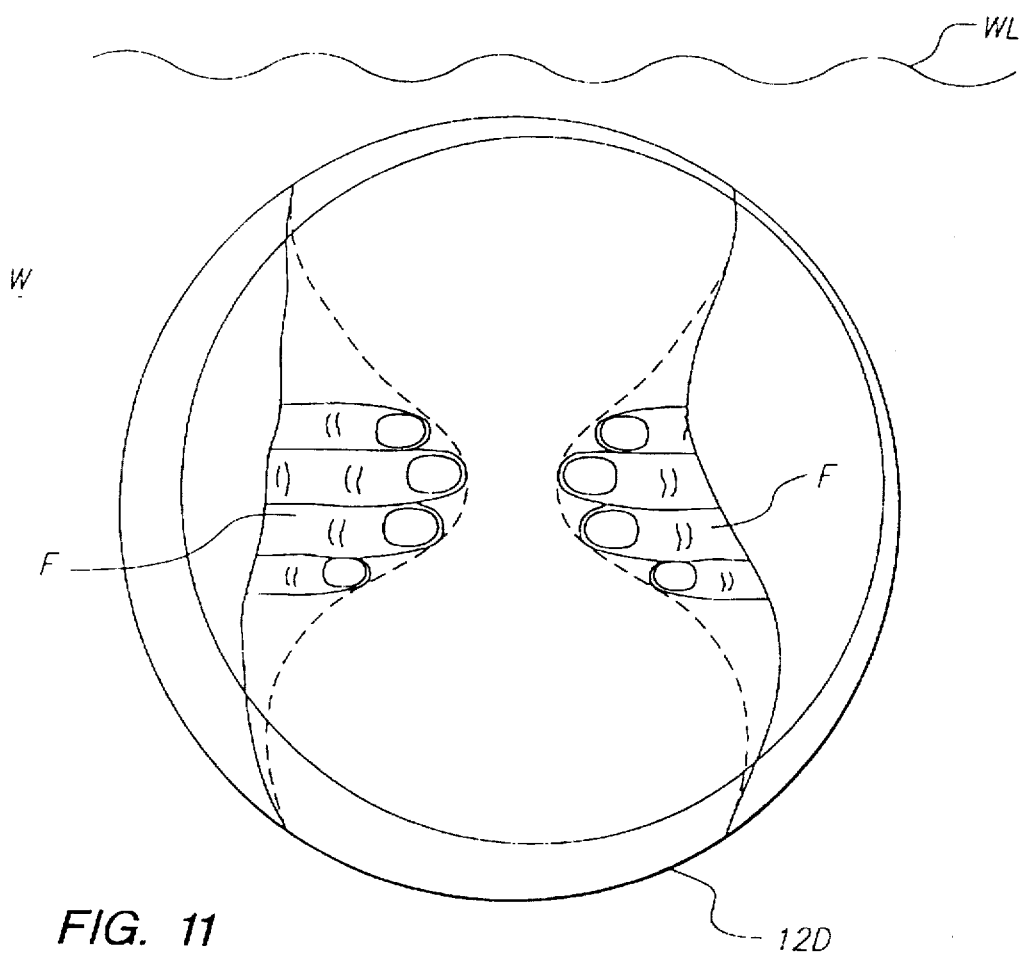
FIG. 11 depicts front views of the breast during an examination that shows the fingers from each hand in an opposed juxtaposition.
Figure 12A:
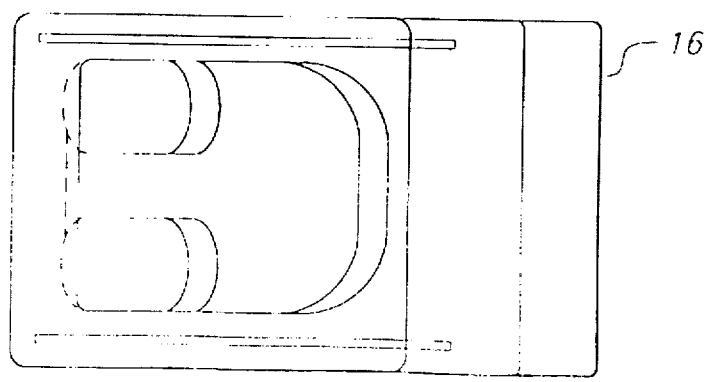
FIGS. 12A, 12B, 13, 14, 15 and 16 offer top and cut-away side views of various floatation spa tubs 16 which may be used to practice the Finger Walk$^{SM}$ examination method.
Figure 12B:
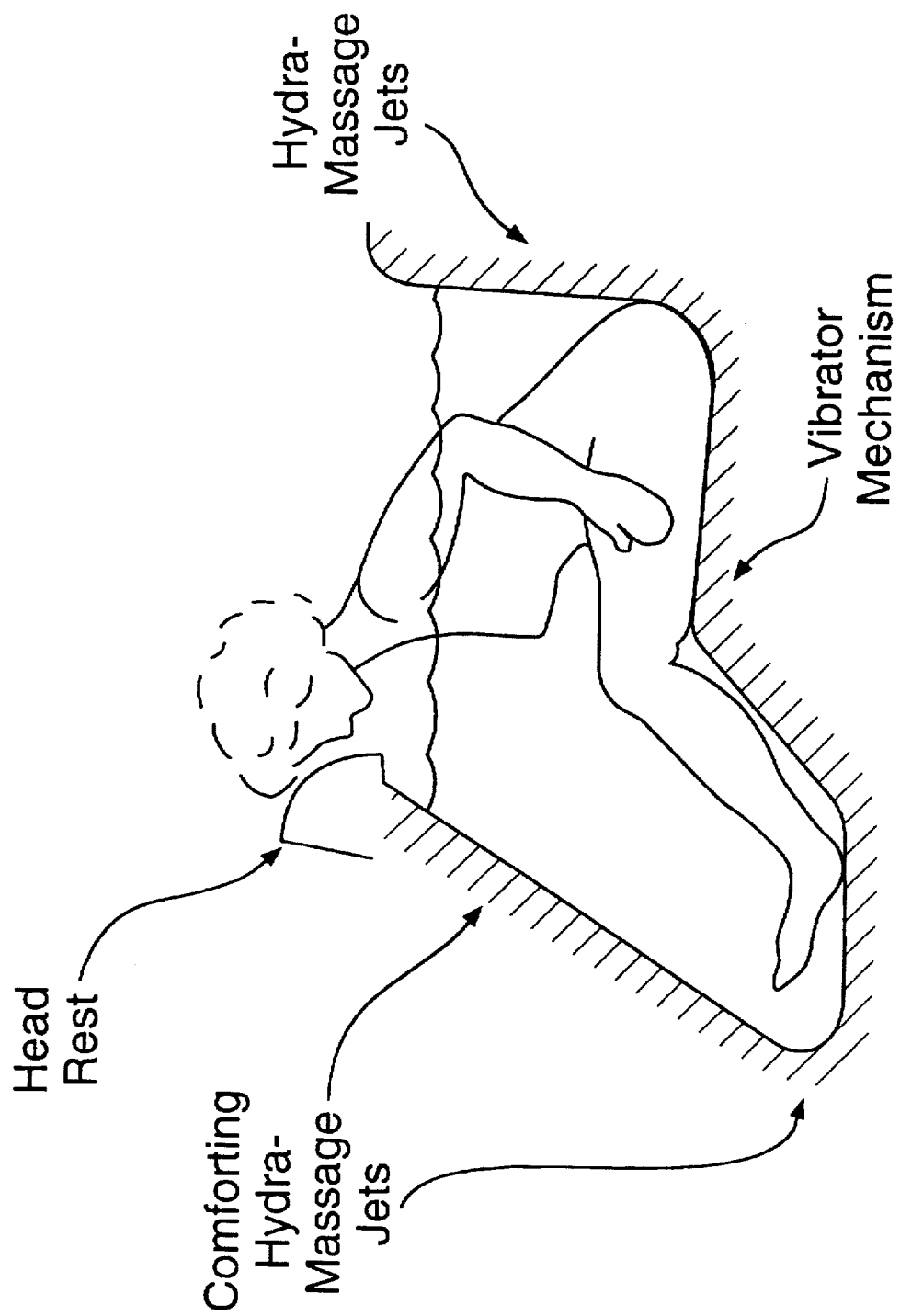
Figure 13:
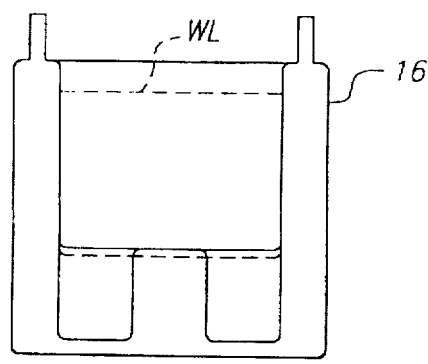
Figure 14:
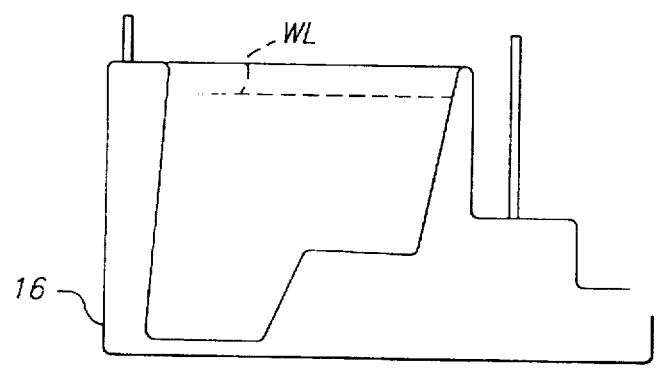
Figure 15:
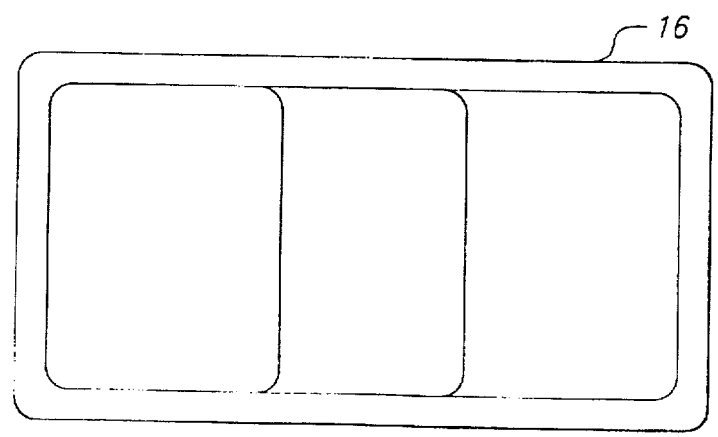
Figure 16:
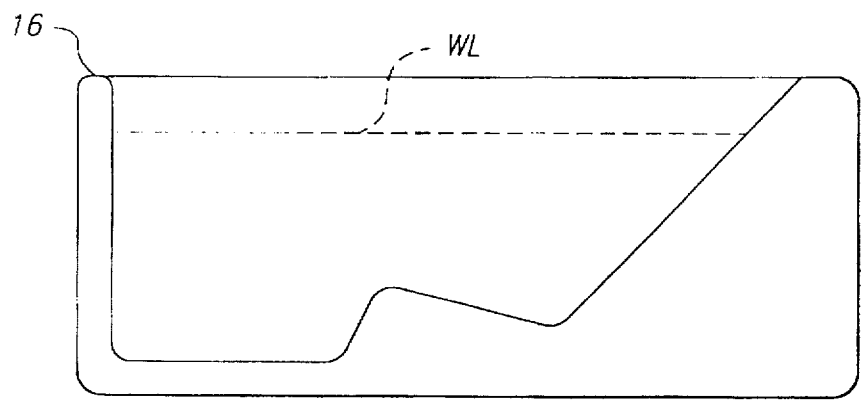

FIG. 11 depicts front views of the breast during an examination that utilizes several fingers from each hand. In general, the three index fingers are employed to perform an examination.

Advantages of the Finger Walk$^{SM}$ Method

The present invention is designed to stimulate the flow of lymph fluid in breast, as well as to encourage blood flow through the capillaries of the breast. The Finger Walk$^{SM}$ may break up lumpy clusters and make breast tissue more pliable. These effects may compensate for a patients's lack of adequate exercise.

Unlike conventional two-dimensional body massage techniques, the Finger Walk$^{SM}$ Method may help clear up lumpiness and generally make the breast more pliable. The stimulation of the flow of the lymphatic system may inhibit maladies in the body tissue adjacent to the lymph ducts. The lymphatic duct system does not have a circulating pump to drive the lymph fluid through the duct system to the lymph nodes. The lymph system depends upon the motion of the body in the form of work or exercise to cause the muscles to impose forces upon the lymphatic duct system. These forces, in turn, drive the lymph fluid to flow through the body to provide a cleansing function. Insufficient exercise may limit the flow of this fluid and provide inadequate cleansing.

It is reasonably well known that women athletes have a considerably lower incidence of breast cancer than the general population. This would imply that their athletic motions stimulate the flow of not only blood through the breast, but also the flow of the lymphatic fluids through the same area. This activity may promote better health in this area of the body and could potentially lower the incidence of cancer.

In addition to stimulating the flow of body fluids in the breast tissue, the Finger Walk$^{SM}$ Method may also have the beneficial effect of realigning the internal structure of the breast into its natural desired position. This realignment could be similar to an intestinal disorder caused by an intestine that has become displaced or contorted. The realignment of the tissues of the breast may improve the health of the breast and reduce the incidence of lumps and other breast abnormalities.

Apparatus Used to Practice the Finger Walk$^{SM}$ Method

Figure 17:
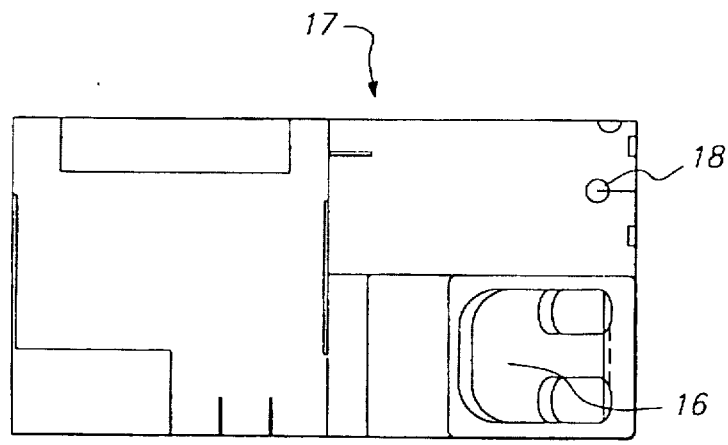
FIGS. 17, 18 and 19 furnish plan and elevational views of various embodiments of a modular spa facility 17 that includes both a tub 16 and a shower 18 which may be used to practice the present invention.
Figure 18:
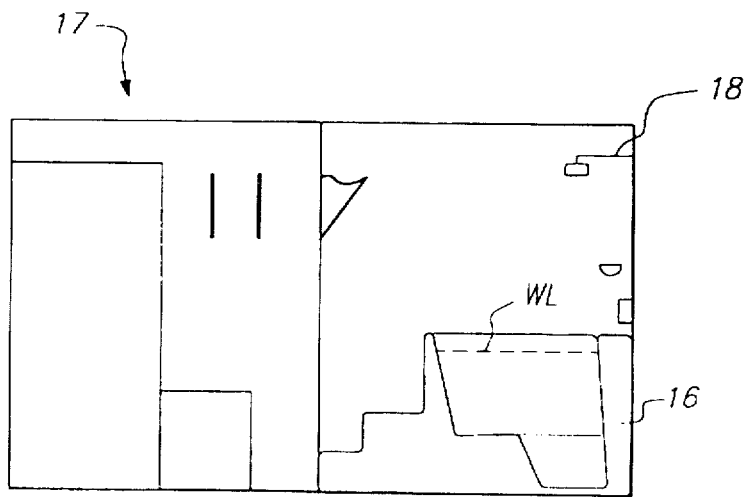
Figure 19:
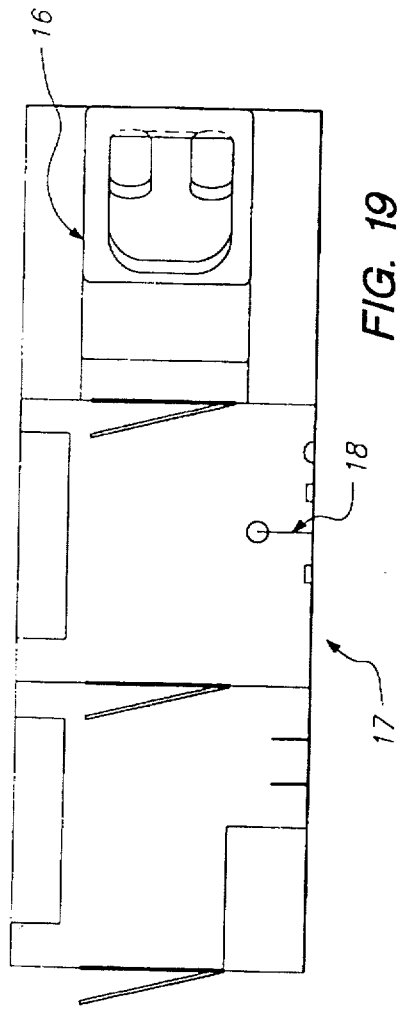

FIGS. 12A, 12B, 13, 14, 15 and 16 offer top and cut-away side views of a floatation spa tub 16 which may be used to practice the Finger Walk$^{SM}$ examination method. FIGS. 17, 18 and 19 furnish plan and elevational views of various embodiments of a modular spa facility that includes a tub 16 and a shower 18 which may be used to practice the present invention. FIG. 19 also shows a dressing room facility which may be used by the patient.

Figure 20:
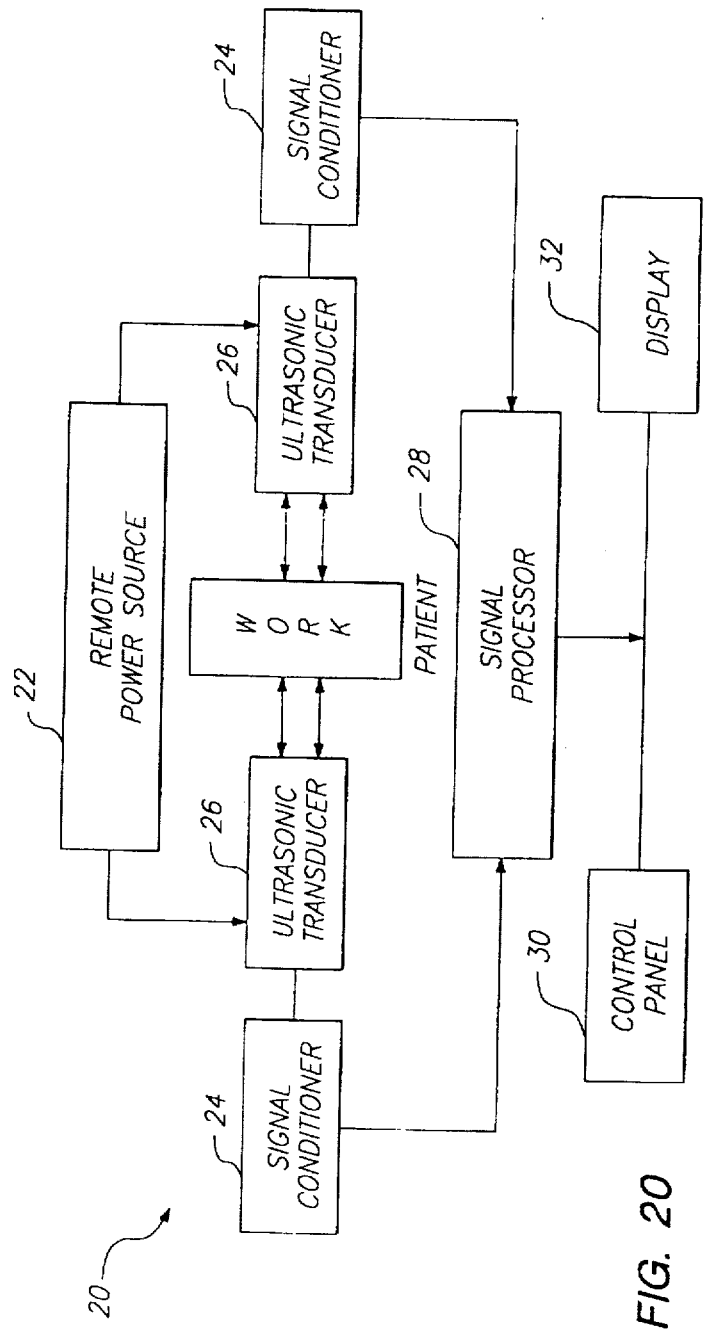
FIG. 20 is a schematic block diagram that depicts the ultrasonic apparatus that may be used to implement the invention.

FIG. 20 is a schematic block diagram that depicts apparatus that is well known to persons ordinarily skilled in the ultrasonic imaging art that may be used to implement the invention. Diagram 20 includes a remote power source 22 coupled to ultrasonic transducers 26. A signal is produced by the transducers 26 which is processed by signal conditioners 24 and signal processors 28 to form an image of the patient's body tissues. The image is generated on a display 32. The electronic equipment is operated by switches on a control panel 30.

Figure 21:
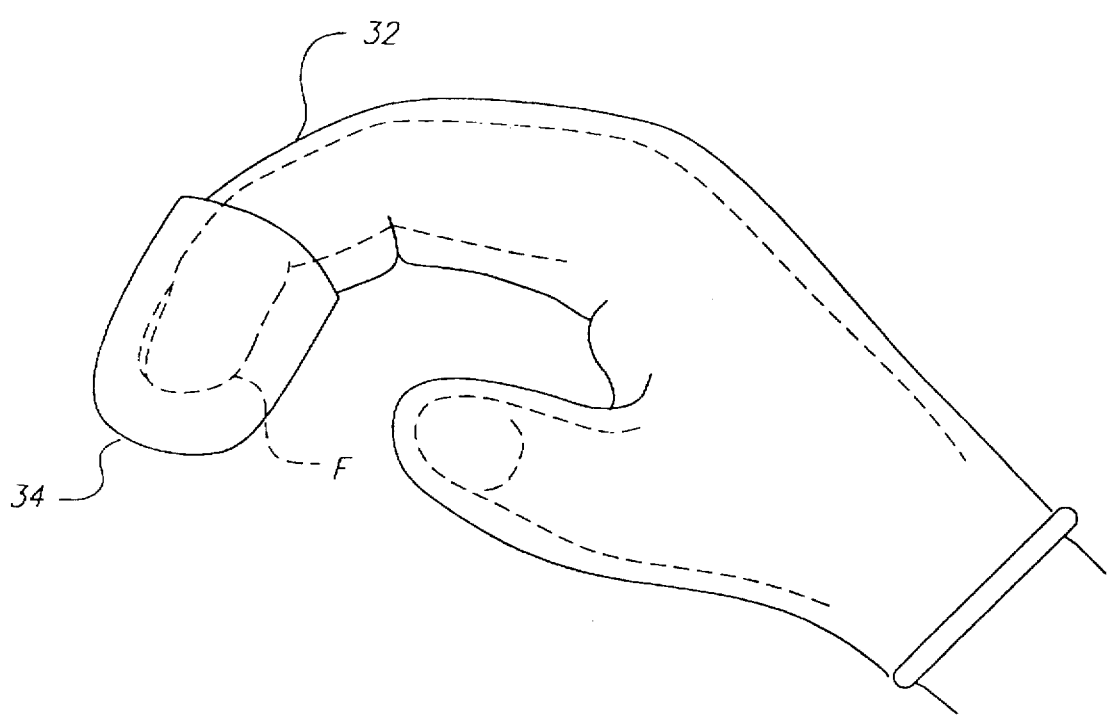
FIG. 21 is a schematic view of an ultrasonic transducer mounted in the finger of a glove that may be used to implement the invention.

FIG. 21 is a schematic view of an ultrasonic transducer mounted in the finger cup 34 of a glove 32 that may be used to implement the invention.

Figure 22:
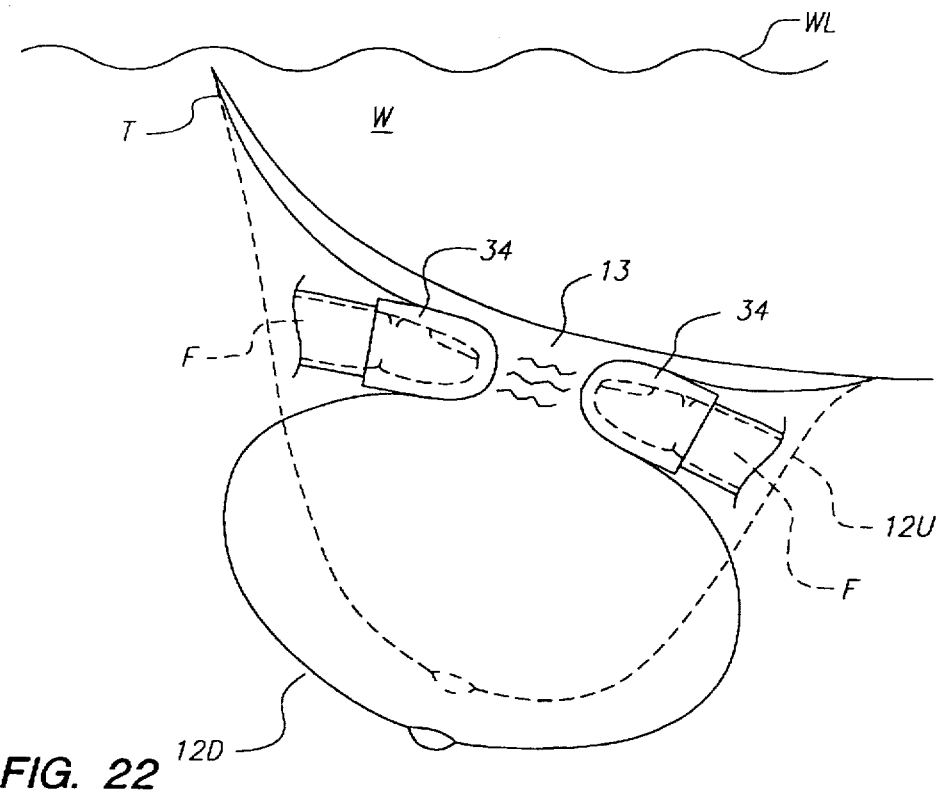
FIGS. 22 and 23 are superimposed views of a breast in both undeflected and deflected conditions. The view in each figure which represents the breast in floatation shows the tissue in a deflected condition during an examination that utilizes the transducer shown in FIG. 21.
Figure 23:
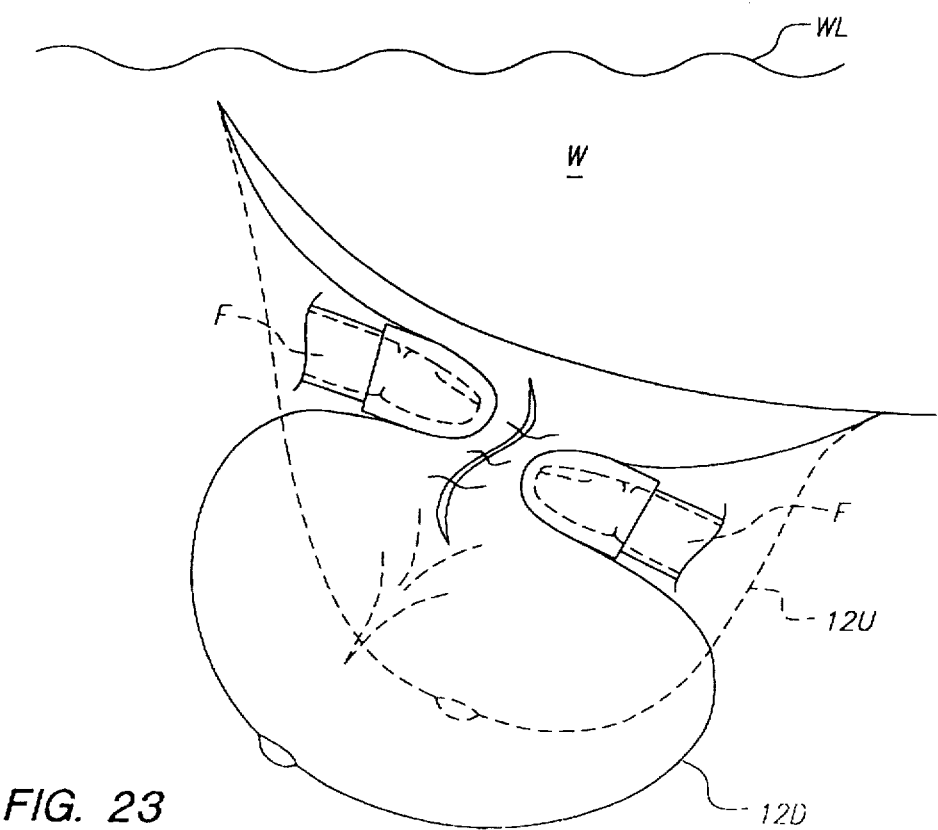

FIGS. 22 and 23 are superimposed views of a breast in both undeflected 12U and deflected 12D conditions. The view in each figure which represent s the breast in floatation shows the tissue in a deflected condition during an examination that utilizes the finger cup transducer 34 shown in FIG. 21.

Advanced Finger Walk[SM] Methods

Figure 24:
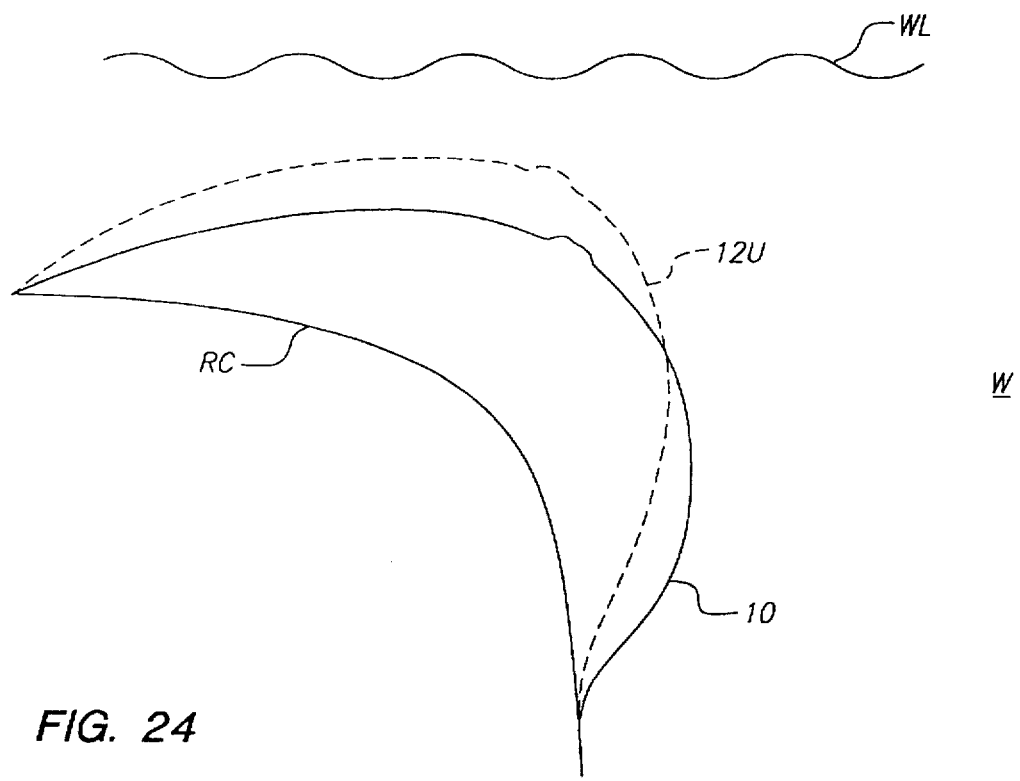
FIG. 24 provides views of a female breast while the patient is in a supine position.
Figure 25:
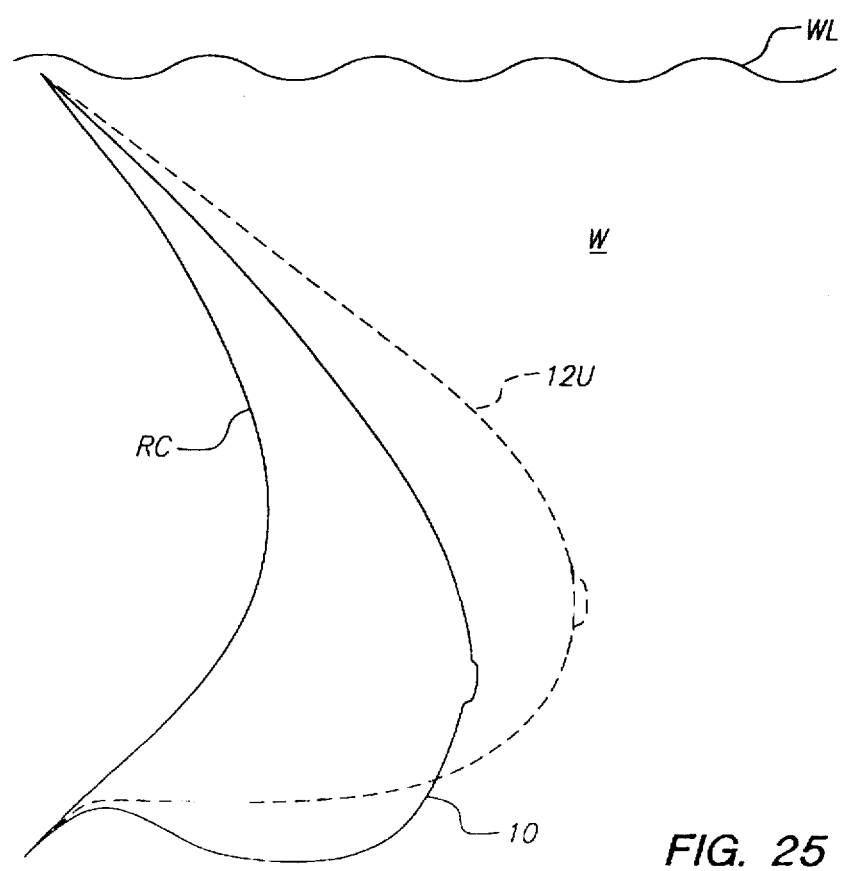
FIG. 25 provides views of a female breast with the patient in a supine position, but with the rib cage rotated outward approximately forty-five degrees.

FIG. 24 presents two different views of a female breast while the patient is in a supine position, with the patient flat on her back. As best seen in FIG. 24, without being immersed in water W, the breast would normally occupy the position indicated by reference character 10. When the breast is immersed below the water line WL, it is levitated and occupies the position indicated by reference character 12U. In either case, the contour of the rib cage is represented by reference character RC. FIG. 25 furnishes a pair of views of a female breast in both the normal 10 and levitated 12U positions when the patient is in a supine position, but with the rib cage rotated outward approximately forty-five degrees. This position is especially useful for examining the pectoral area under the arm pits after a breast is gently moved to one side with one hand while probing is accomplished with the other hand.

Figure 26:
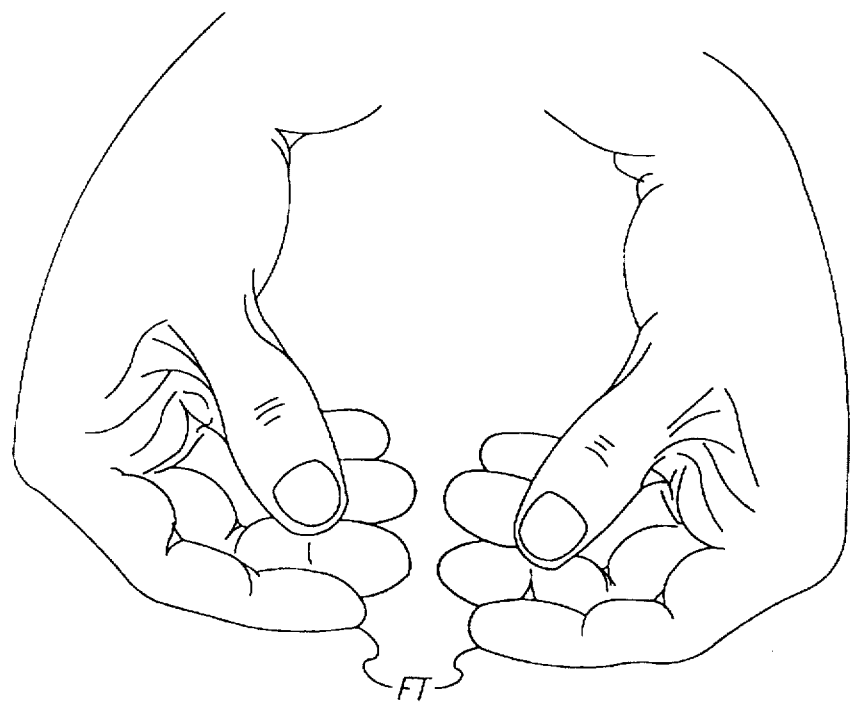
FIGS. 26, 27 and 28 illustrate the positions of the examiner's hands and fingers during the examination procedure embodied by the present invention.
Figure 27:
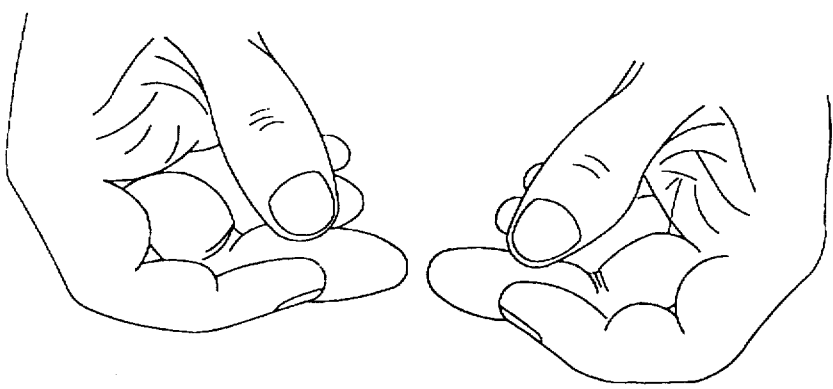
Figure 28:
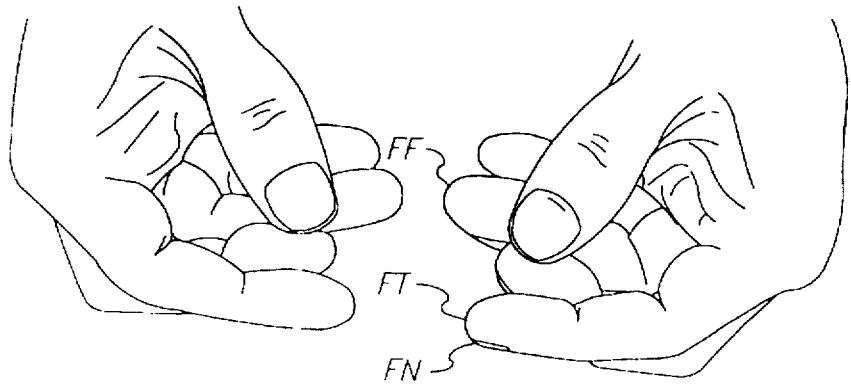

FIGS. 26, 27 and 28 reveal the placement and motion of the hands and the fingers according to a preferred embodiment of the present invention. In FIG. 26, the fingers F are generally in-line and occupy a normal extended position. In FIG. 27, the middle fingers F of both hands are extended toward each other. In FIG. 28, the middle fingers F move in and out slightly in a gentle repetitive motion, permitting the internal breast structure to readjust to penetration by the fingers. This readjustment enhances the ability of the examiner to detect abnormalities. FIG. 28 also identifies the area of the examiner's finger F that is used to perform the Finger Walk[SM] Method. The present invention relies on the enhanced sensitivity of the small portion of the finger tip FT that lies immediately below the fingernail FN. The flat portion FF of the finger, which is located near the whorl of the fingerprint, is less sensitive than the finger tip FT, and is therefore not used to perform the Finger Walk[SM]. Unlike previous breast examination techniques that employ the rotating action of the flat portion of the fingers, the present invention utilizes a series of palpating motions.

Figure 29:
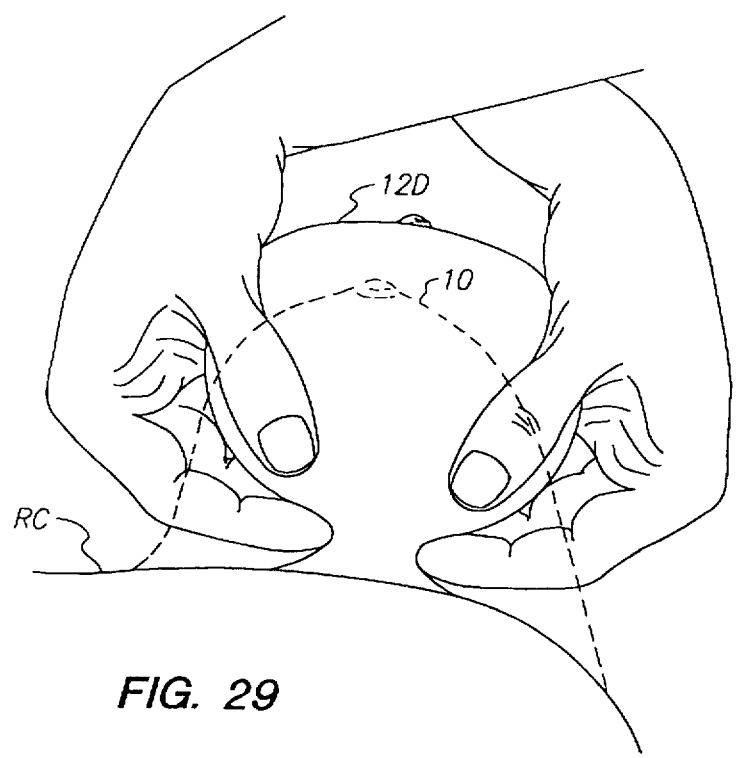
FIGS. 29, 30, 31, 32 and 33 comprise a series of overhead views of hand and finger positions that illustrate the Finger Walk$^{SM}$ method. In these figures, the right breast is immersed in a floatation bath with the patient in a generally upright position.

FIGS. 29 through 33 supply a sequence of illustrations of a Finger Walk[SM] procedure that is conducted while the patient is in an upright position, and leaning slightly forward. The perspective of FIGS. 29 through 33 is from a point above the patient's head, looking down into the water bath at her immersed breasts. FIG. 29 reveals a female breast on the right side of the torso in normal 10 and levitated and deflected positions 12D. A portion of the rib cage RC is shown along the base of the breast. FIG. 29 is an overhead view, depicting the crossed left and right hands of the examiner as he or she uses the fingers of both hands to constrict the lower portion of the breast. In FIG. 29, the fingertips are move progressively from the rib cage out toward the nipple. The examiner palpates the tissue by stroking the breast using very gentle pressure. This procedure may be repeated several times. Initially, this three-dimensional palpation may be utilized once or twice. Eventually, the breast structure may become more pliable and these steps can be repeated more often.

Figure 30:
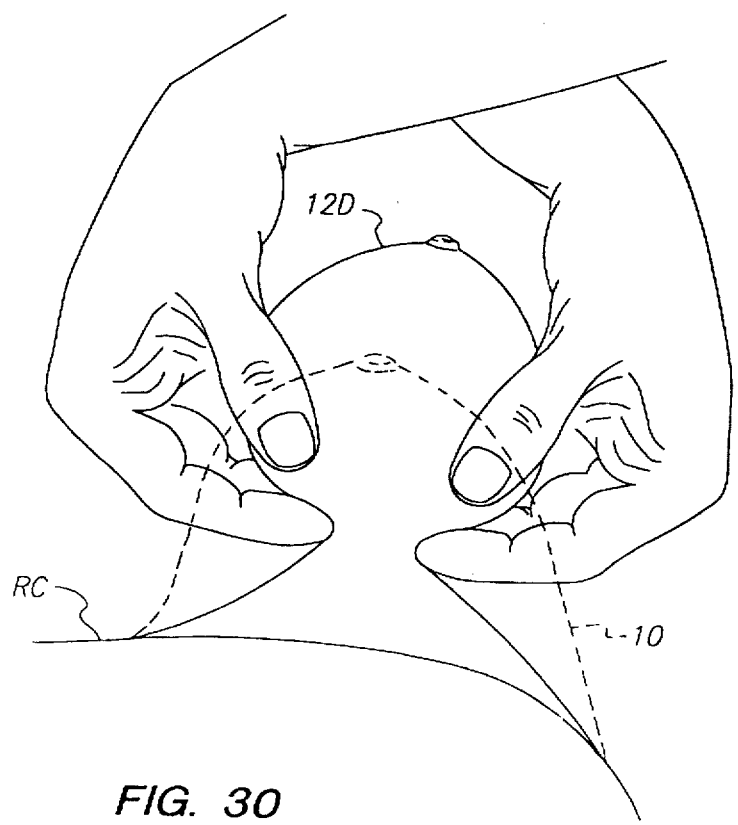
Figure 31:
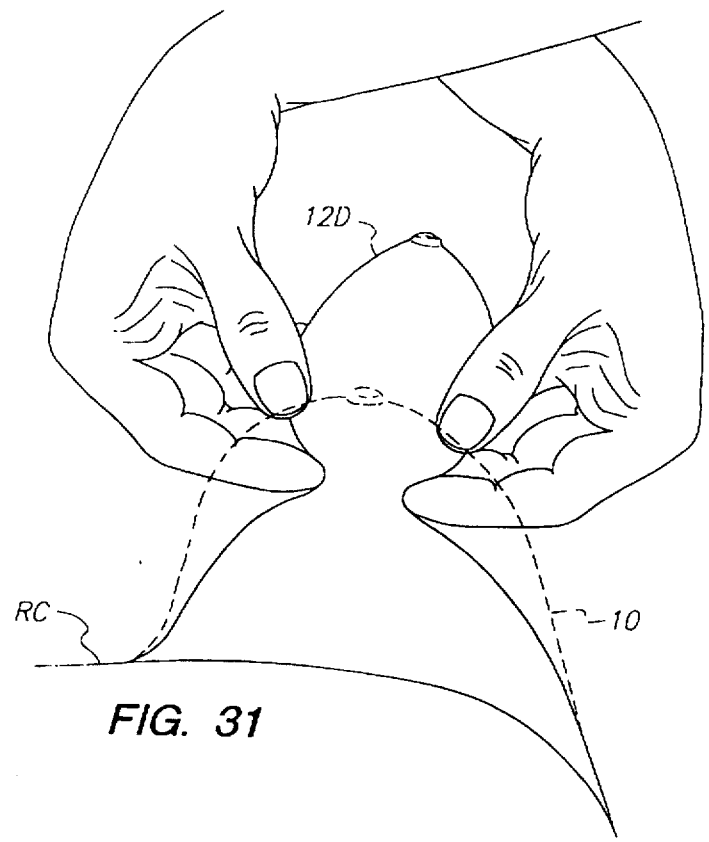

FIG. 30 shows the next stage of the Finger Walk[SM], depicting the breast in an extended position 12D. FIG. 31 offers a view of the breast in a constricted position 12D. In FIG. 30, the opposing finger tips are shown as they approach the midway position of the breast. The internal structure has undergone a reasonable change, which allows for greater three-dimensional penetration. As a result, the pressure applied by the fingertips at this stage may be generally reduced. In FIG. 31, the palpating fingertips have nearly reached the full extent of travel toward the nipple and away from the rib cage.

Figure 32:
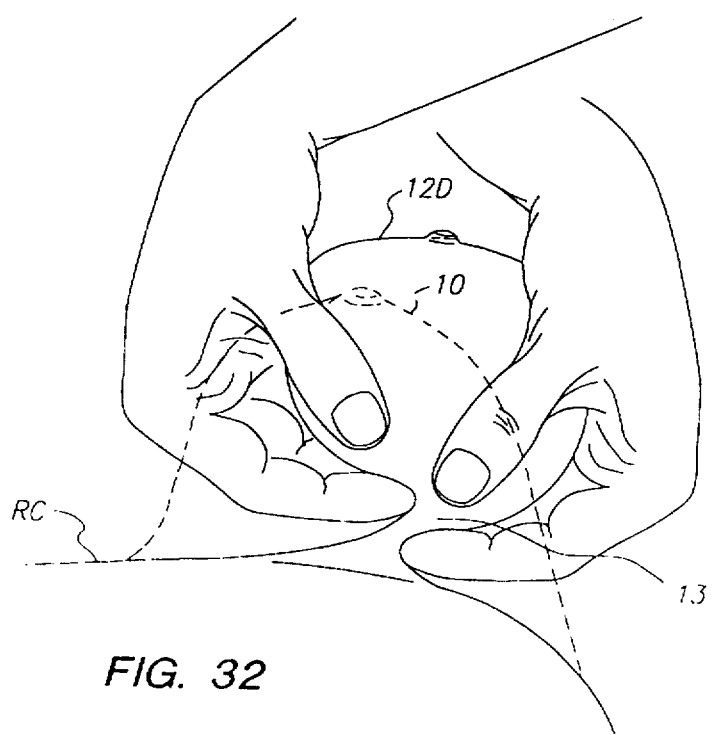
Figure 33:
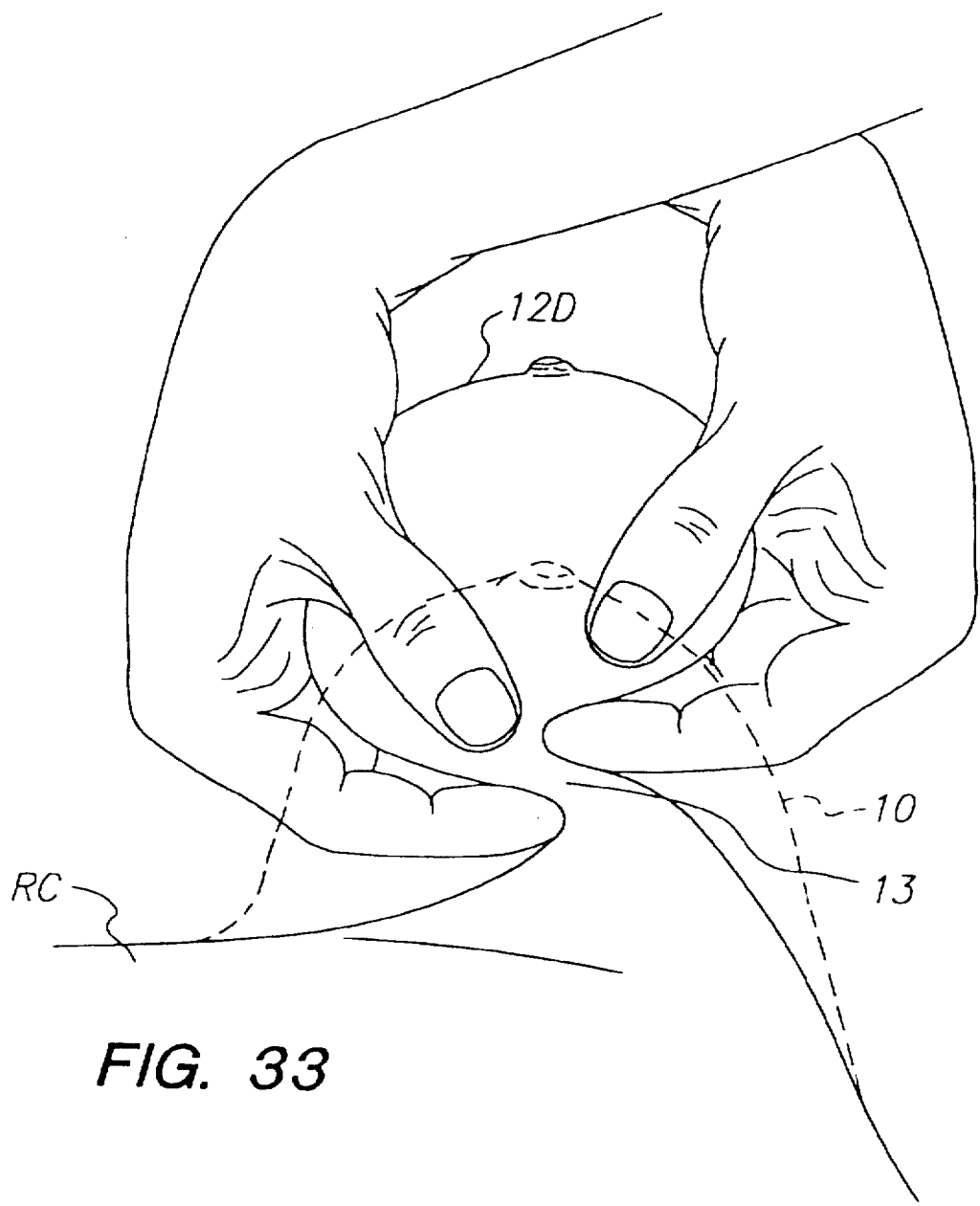

FIGS. 32 and 33 furnish two additional views of the examination process in which the examiner's fingers shape the patient's breast to form an constricted portion or "S-curve" 13 which enhances the sensitivity of the examiner to detect abnormalities. The examiner uses his or her hands so that the S-curve alternates from left to right and back and forth as may be required to perform a thorough examination. This portion of the method of the invention may be effectively employed in persons having larger breast sizes, for example, large C and D cups. The "S" curve and its modifications may be utilized to assist in reformatting the breast internal structure into its desired normal position. Another view of the "S" Curve is portrayed in FIG. 33 at a position midway in the breast. This procedure is similar to the Finger Walk maneuvers used in determining abnormalities. In FIG. 33, the fingertips are used to stroke the tissue rather than to probe the breast.

Figure 34:
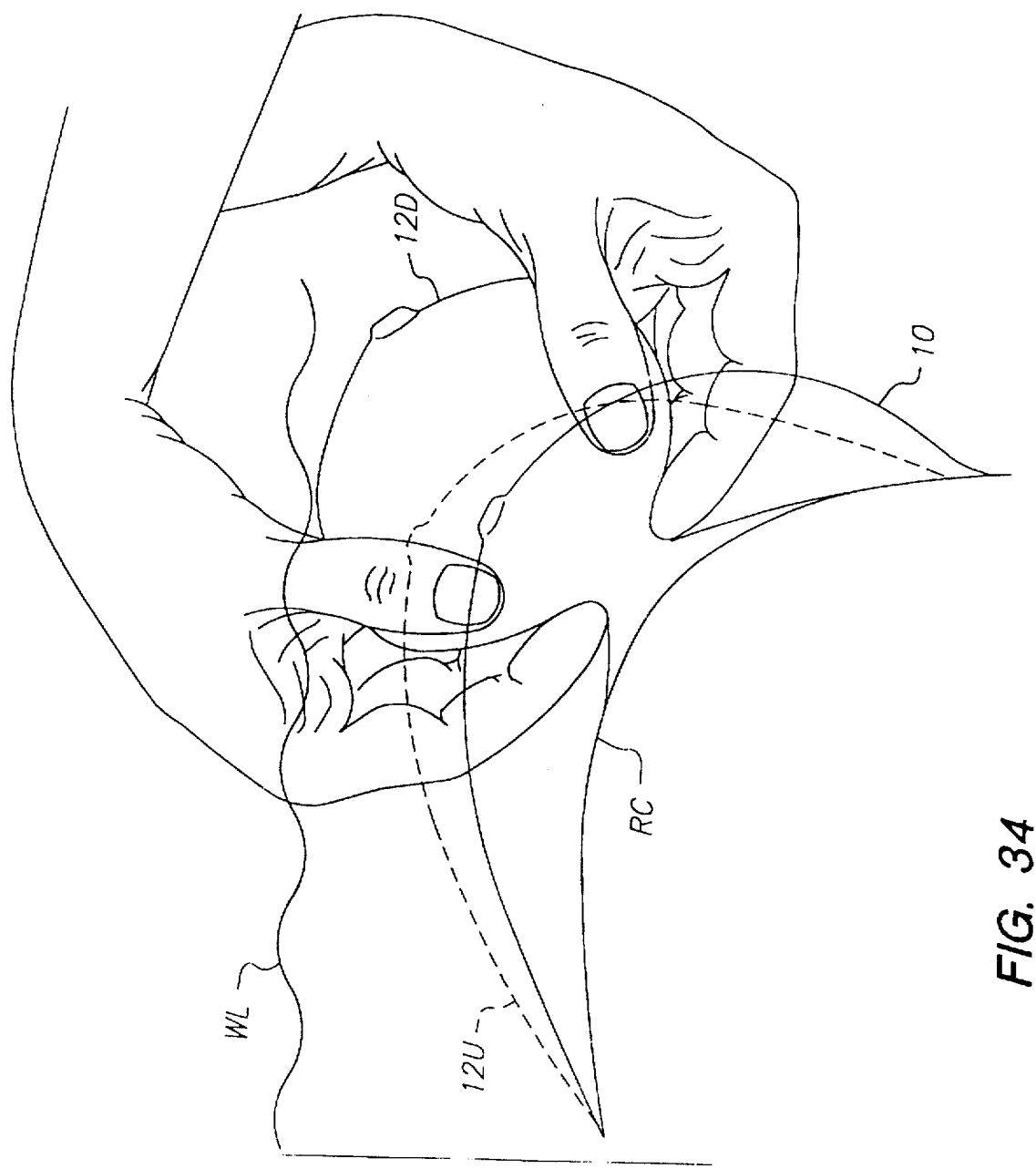
FIGS. 34 and 35 illustrate an examination procedure that is performed with the patient in a supine position with the rib cage rotated outward approximately forty-five degrees.
Figure 35:
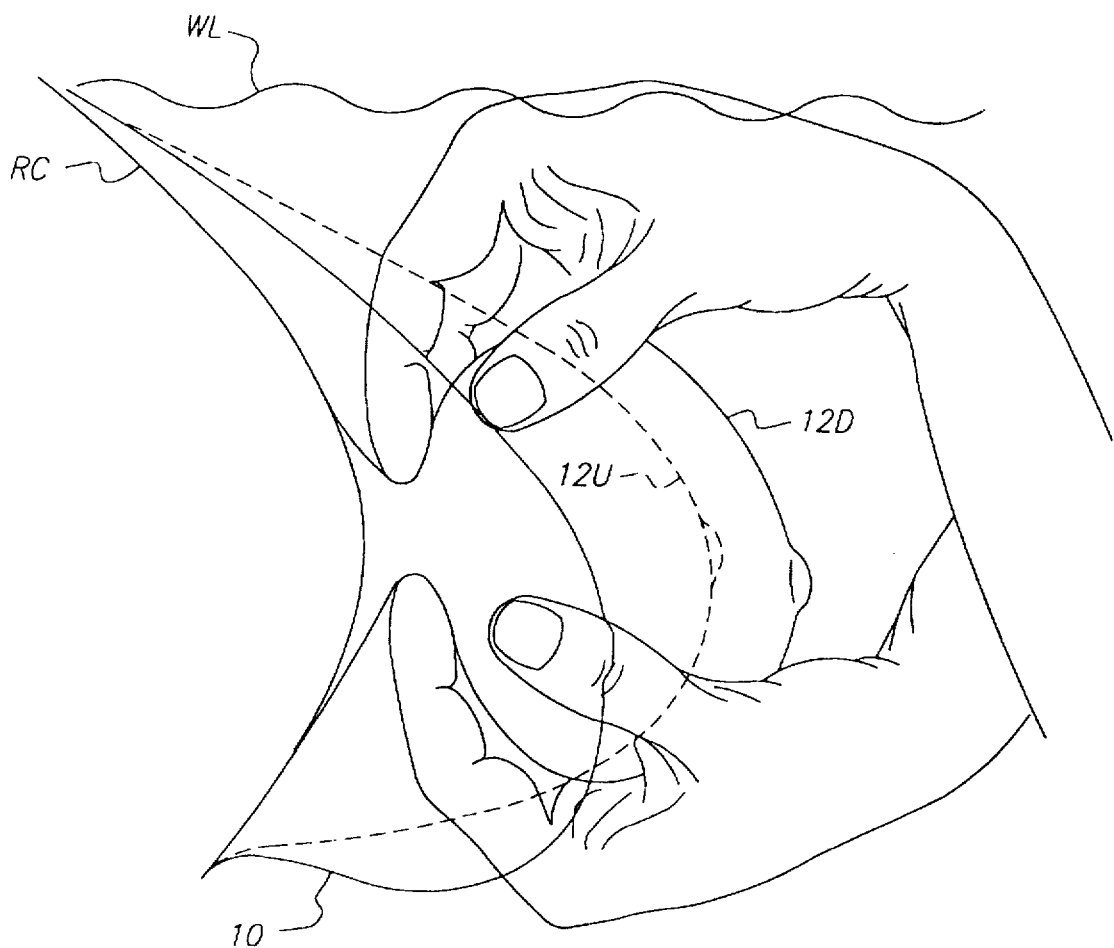

FIGS. 34 and 35 present side views of an examination performed while the patient's rib cage RC is rotated approximately forty-five degrees from a normal upright position. This technique is especially useful for patients having relatively large breasts. The rotation of the rib cage permits access to tissue overlying the lymph nodes and also allows for the examination of the pectoral muscle and tissues around the arm pit.

Figure 36:
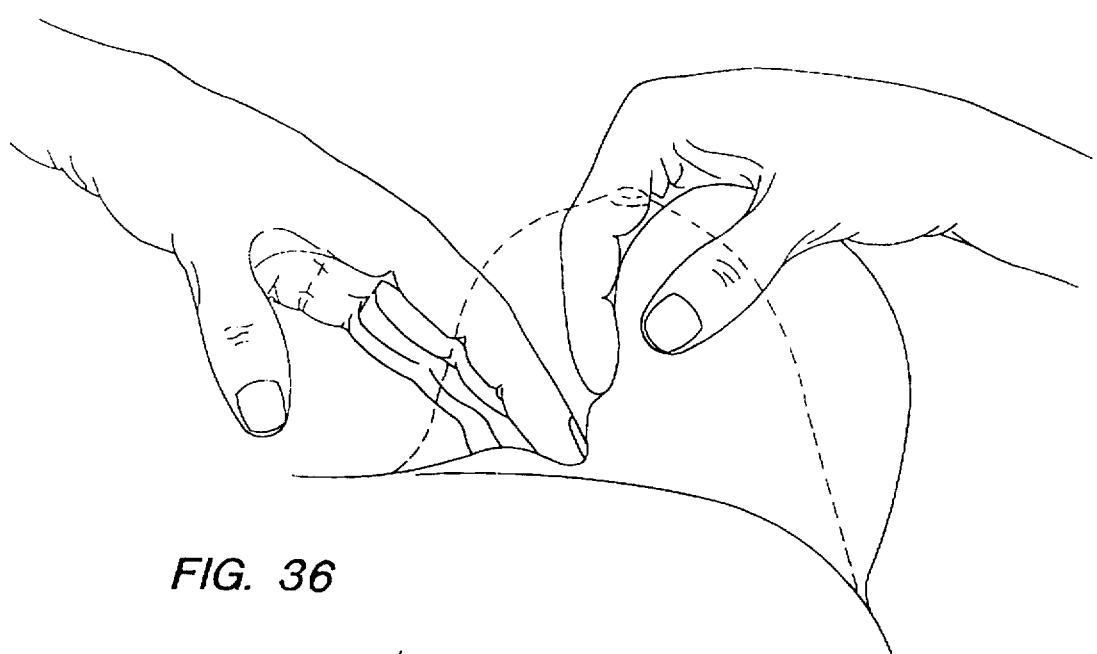
FIGS. 36 and 37 exhibit an examination procedure which is performed with the patient in an upright position.

FIG. 36 is an overhead view of an examination procedure in which the right breast is moved out to the patient's right to permit the examiner to probe the breast tissue near the rib cage with the finger tips of the left hand.

Figure 37:
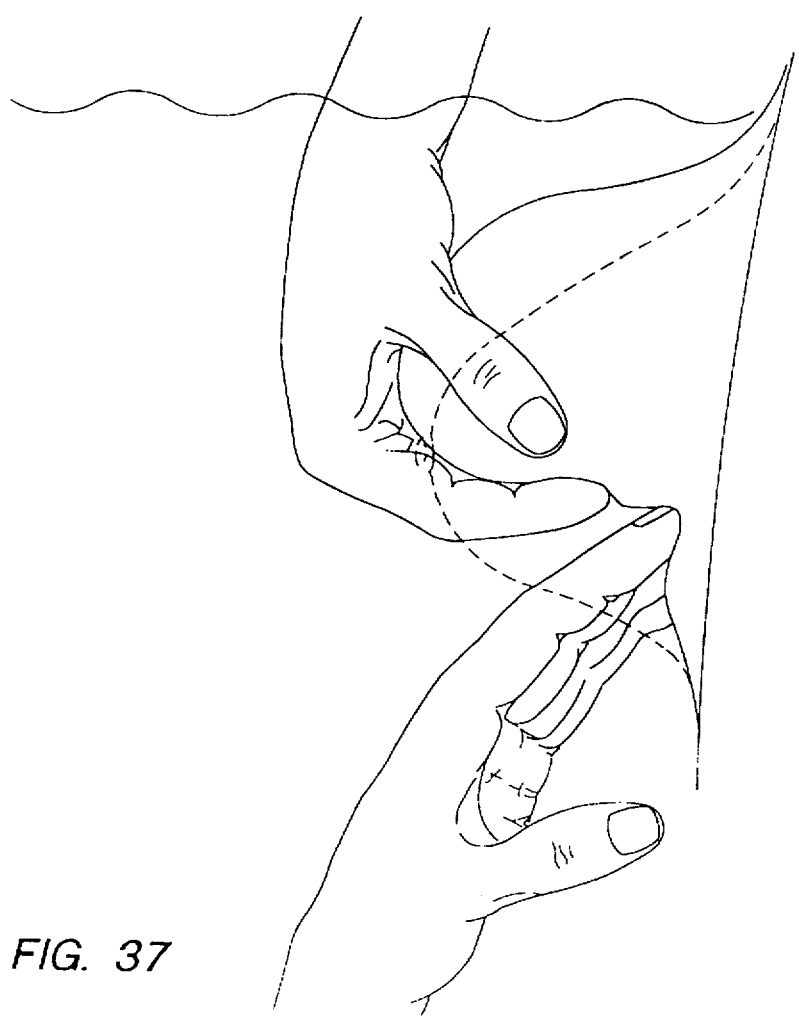

FIG. 37 is a side view which depicts an exam method in which the breast is lifted upward to access the tissue of the lower portion of the breast near the rib cage RC.

An important objective of the Finger Walk[SM] method is to use probing pressure to form a relatively constricted three-dimensional projection of tissue as seen in FIGS. 29 through 37. This projection is achieved by gently working the relaxed and levitated tissues into a shape which is more extended and stretched compared to the normal non-floatation position and shape. After the tissue is constricted and manipulated into a three-dimensional projection, the tissue is palpated using the fingertips (FT), as opposed to the flat portion of the fingers, to detect abnormalities. By using the fingertips instead of the flat portion of the fingers, the patient experiences greater sensitivity by sensing the breast tissue through the tip of the finger as well as the finger nail.

Figure 38:
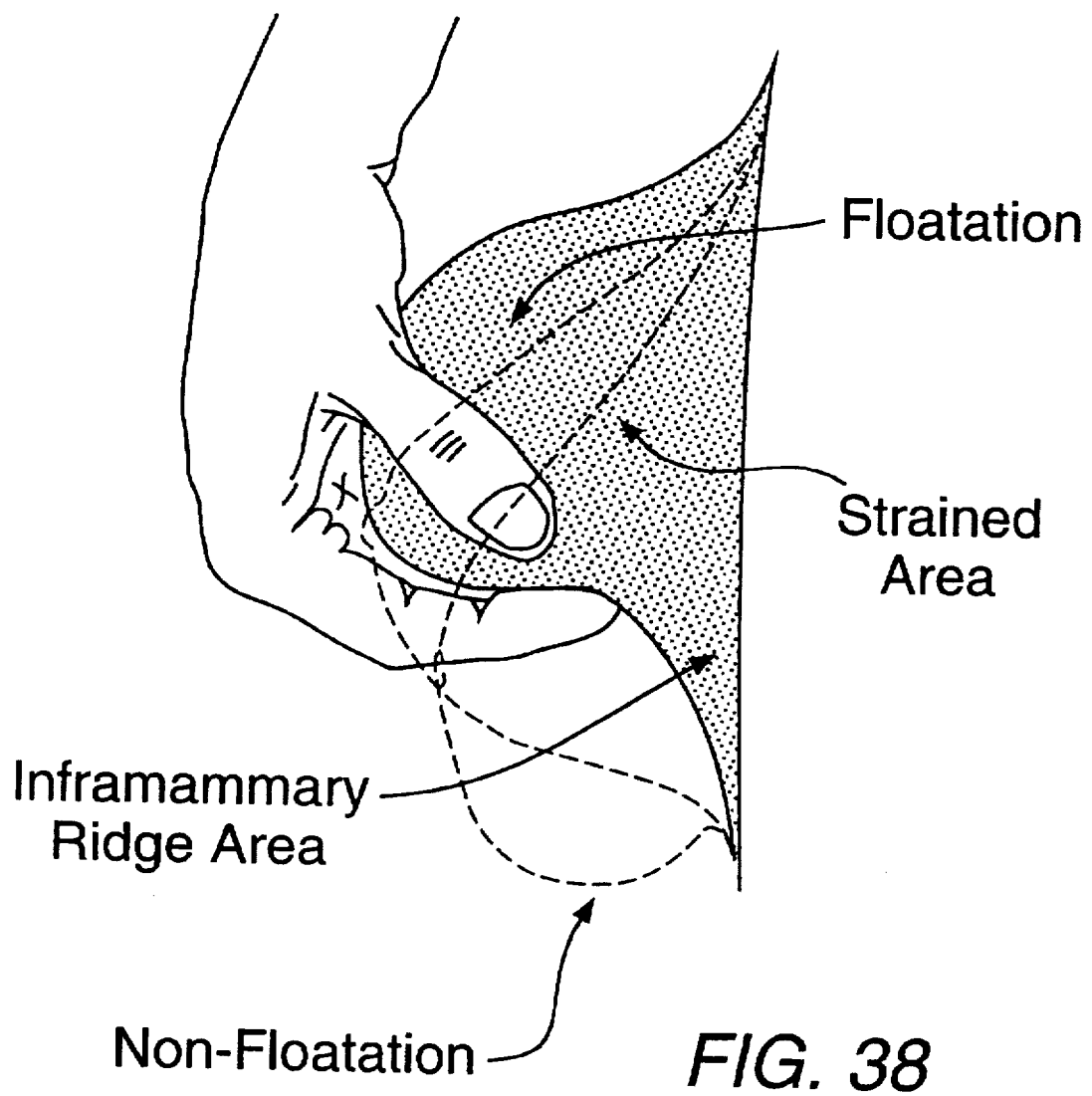
FIGS. 38 and 39 are a side views of a breast with the patient in a floatation bath in a generally upright position.
Figure 39:
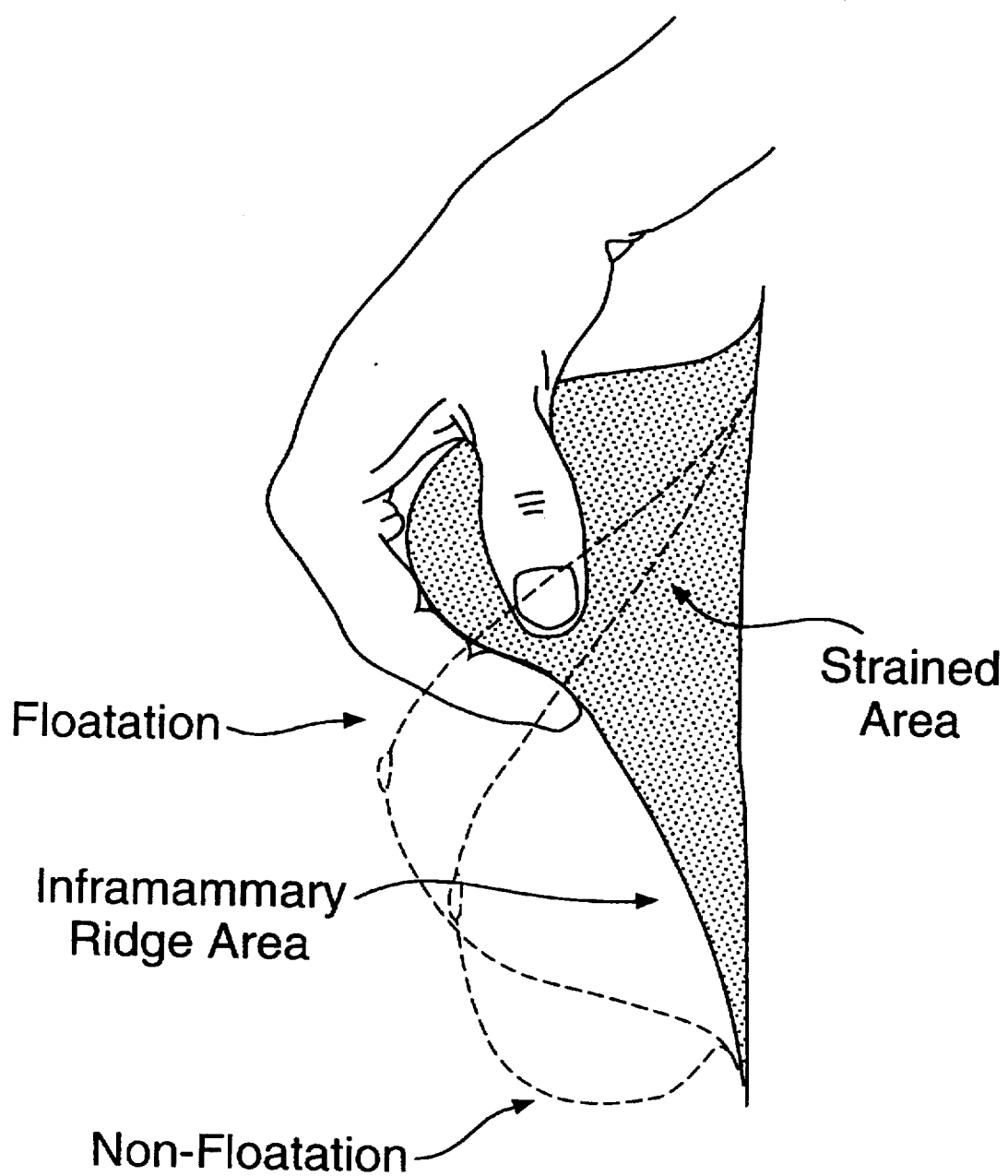

FIGS. 38 and 39 are a side views of a breast with the patient in a floatation bath in a generally upright position. In FIGS. 38 and 39, the floatation forces permit the free motion of the breast, permitting an easy examination of the tissues. The breast tissue near the rib cage is progressively stroked in a upward motion toward the nipple with one hand. In FIG. 39, the breast has been lifted to a position near the upper limit of this palpation procedure.

Figure 40:
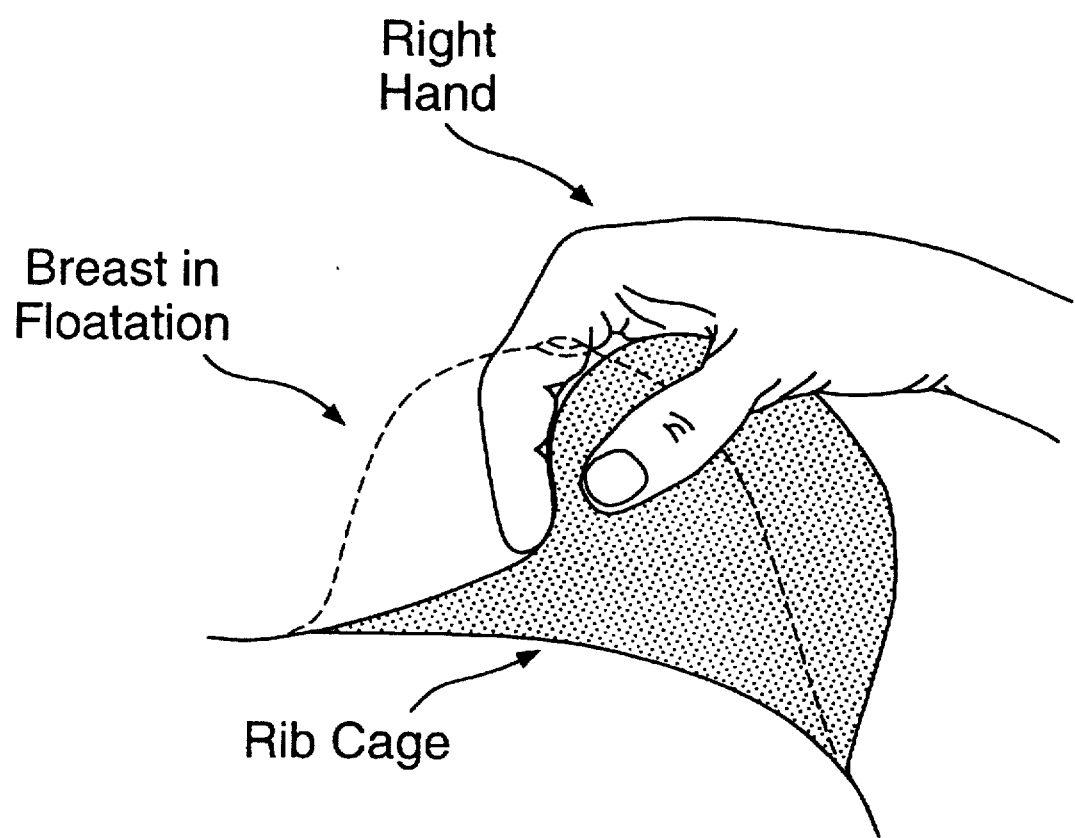
FIGS. 40, 41 and 42 are overhead views looking down on the right breast immersed in a floatation bath.
Figure 41:
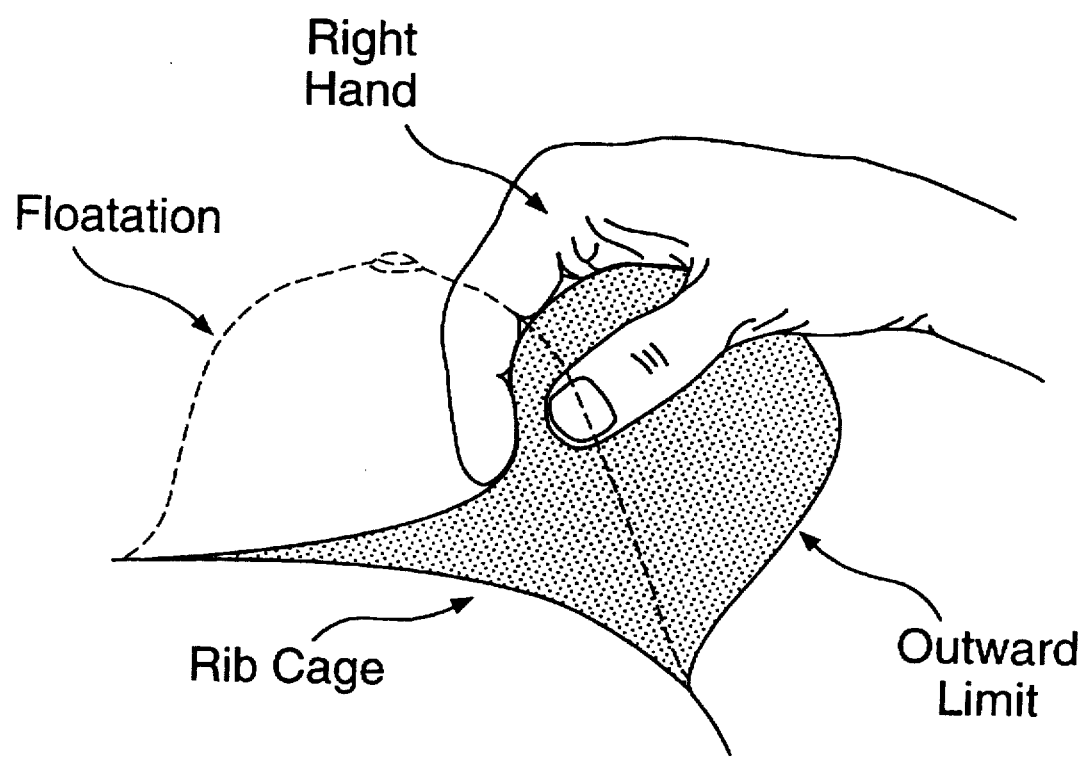
Figure 42:
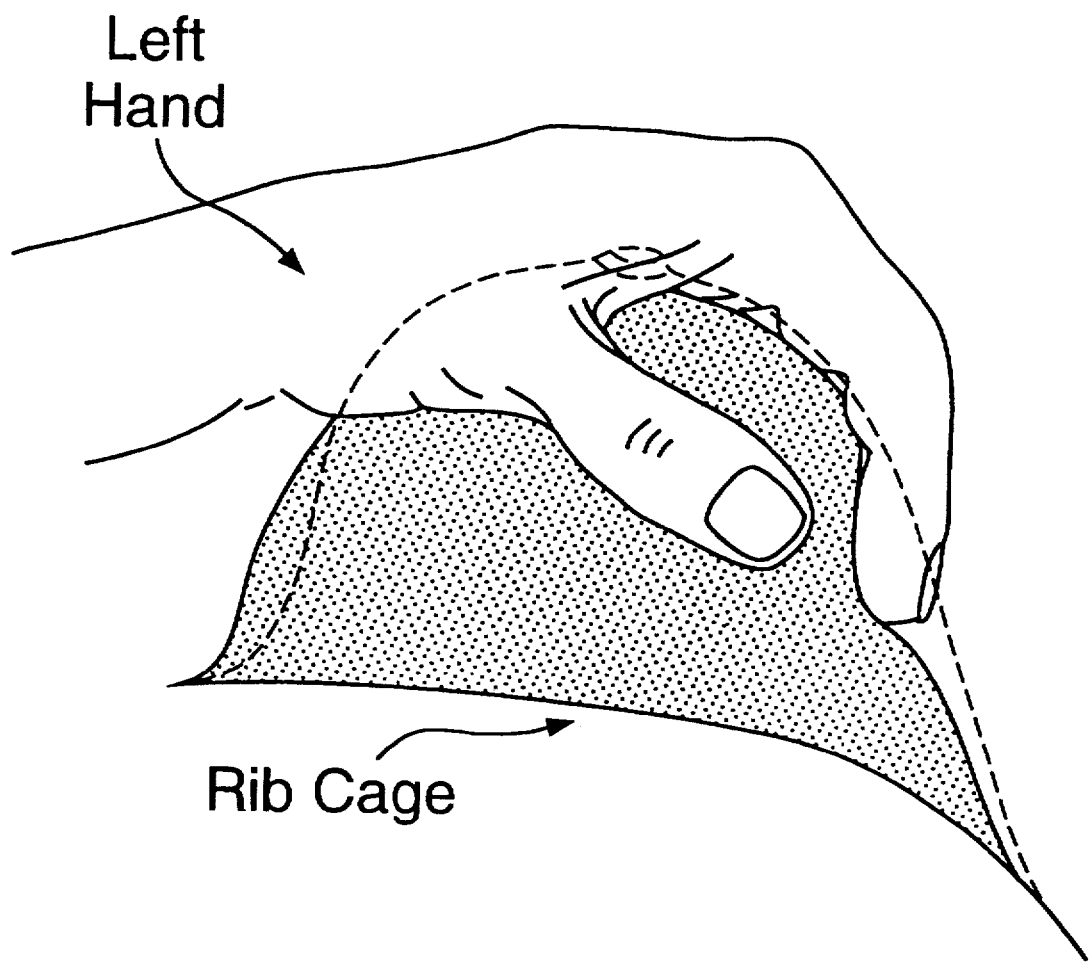

FIGS. 40, 41 and 42 are overhead views looking down on the right breast immersed in a floatation bath. In these figures, the breast is manipulated to relieve stress, to break up clusters in the internal tissue of the breast and to return the internal structure to its natural state. In FIG. 42, the hand is shown as it is gently pulsed in and out and then oscillated in a circular manner to assure that the internal structure finds its natural position. It is generally more comfortable for the patient to use her left hand for the right breast and the right hand for her left breast. This configuration maintains the breasts in an optimal relaxed position with minimal distortion due to arm position, and enables the examiner to massage the lumps residing in emulsified fatty tissue.

Figure 43:
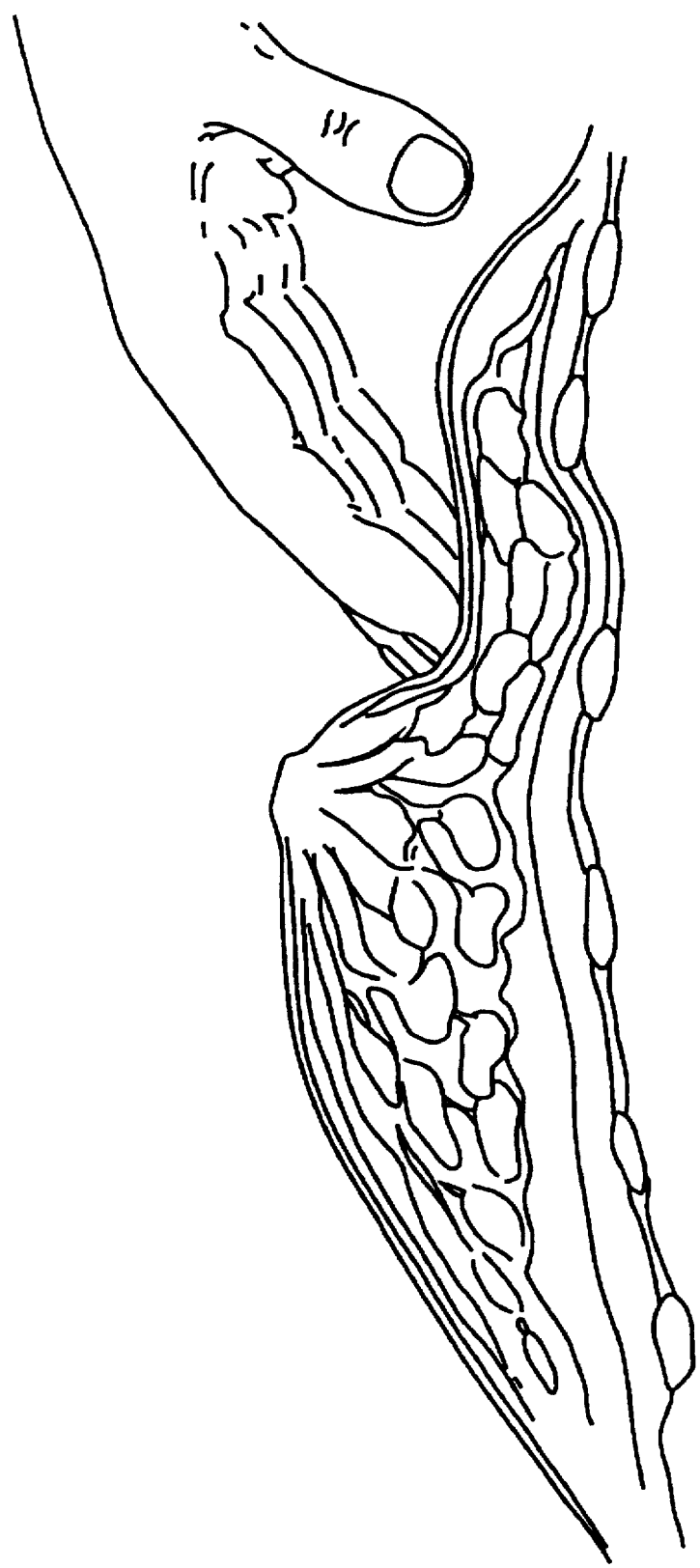
FIGS. 43, 44, 45 and 46 are partial cross-sectional views of the female breast as it would appear while the patient is in the supine position.
Figure 44:
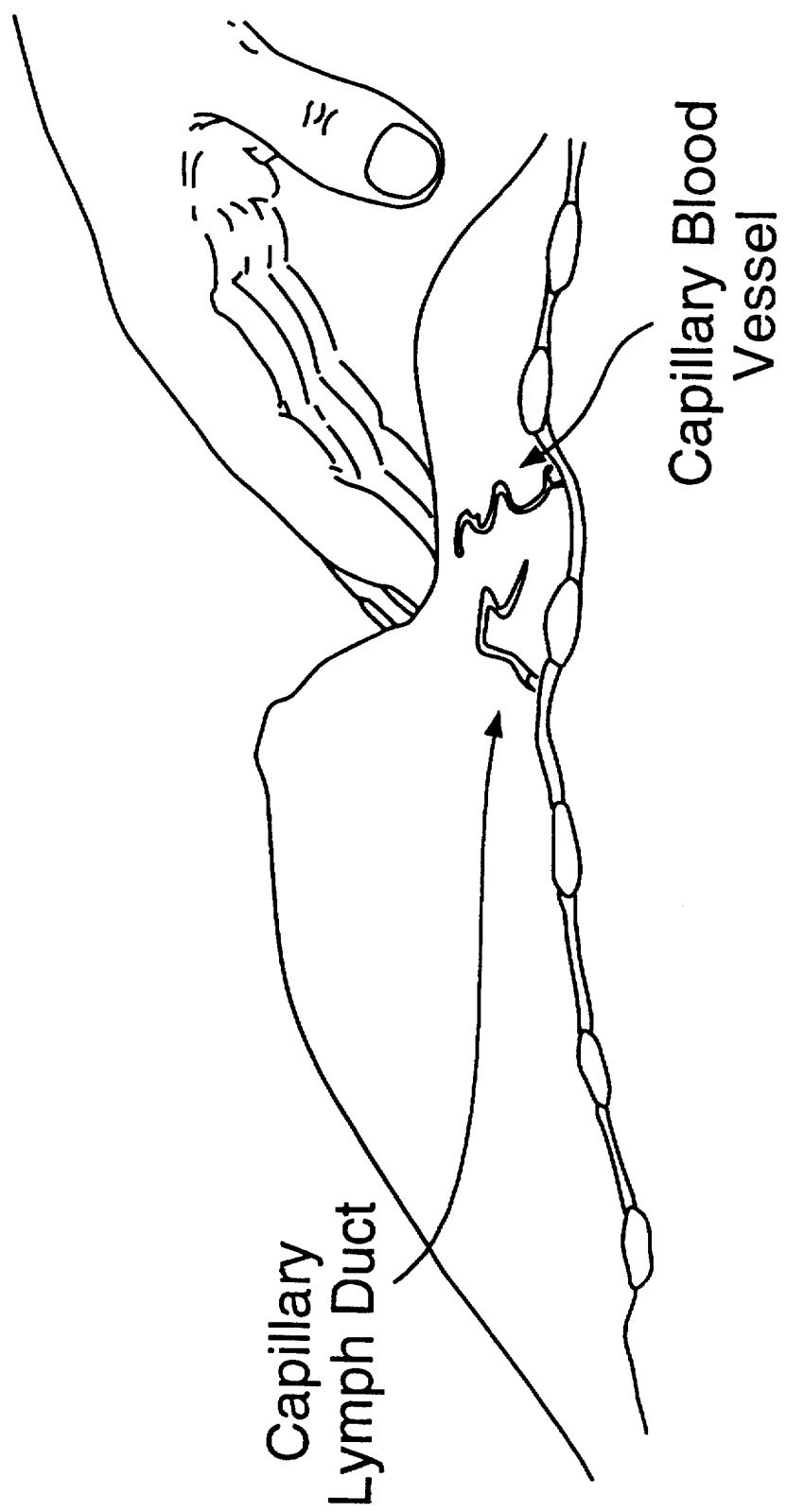
Figure 45:
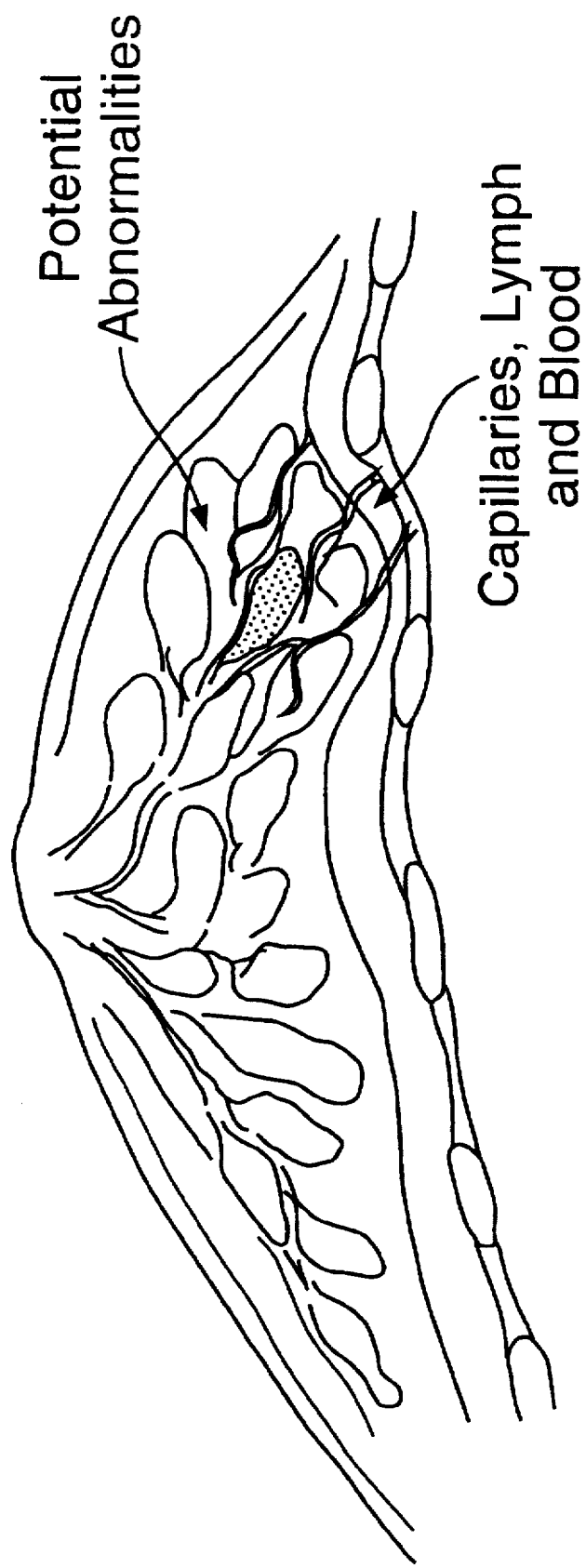
Figure 46:
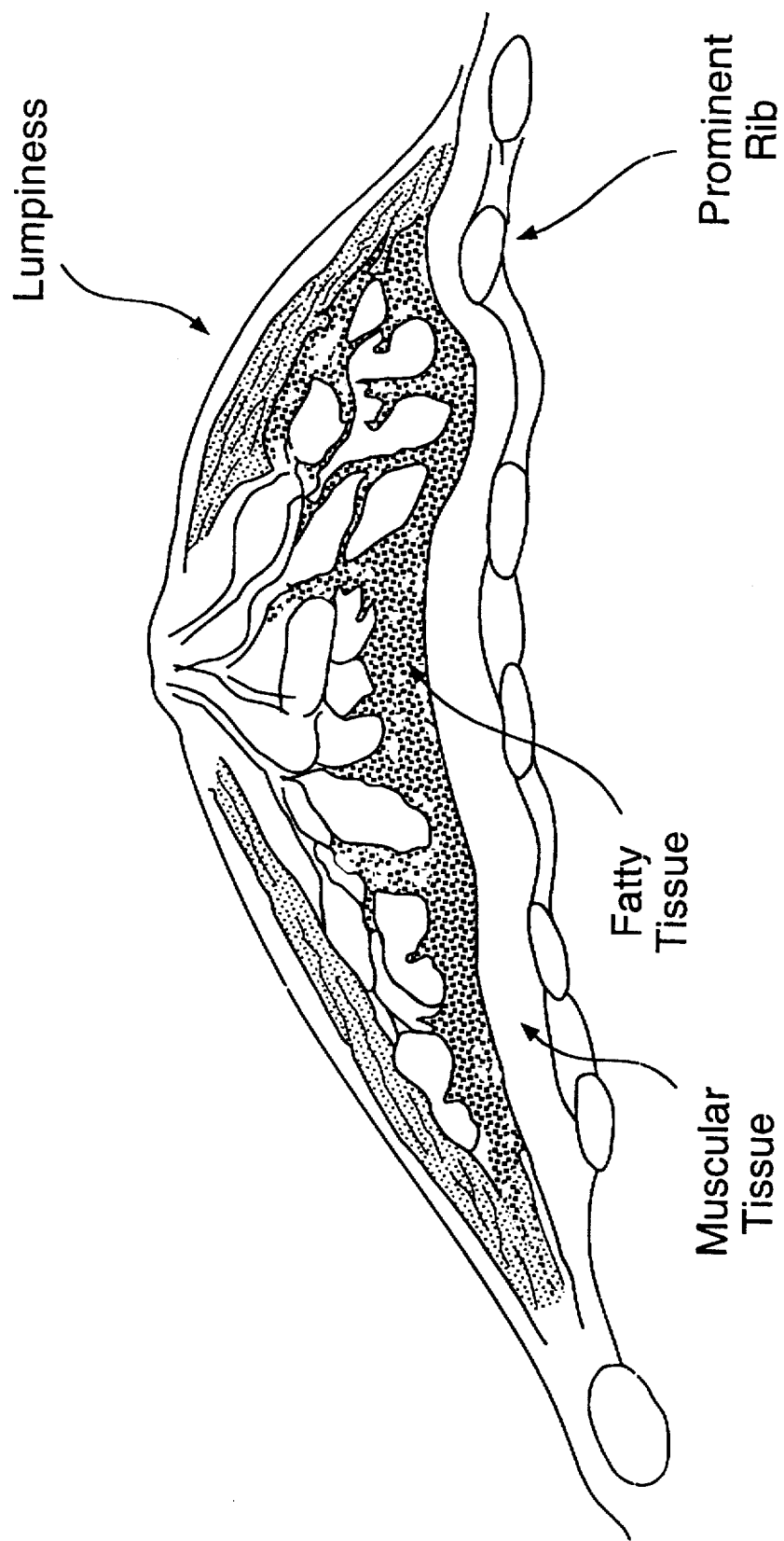

FIGS. 43, 44, 45 and 46 supply partial, cross-sectional views of the breast being massaged while the patient is in the supine position. FIG. 43 depicts the internal structures of the breast that may include lumps or clusters. These lumps or clusters may be held together by fatty tissue or may be entangled by lymph or blood vessels. FIG. 44 shows a capillary lymph duct and a capillary blood vessel. FIG. 45 suggests the structure of a potential abnormality. FIG. 46 reveals lumpy tissues, a prominent rib, and fatty and muscular tissues.

Figure 47:
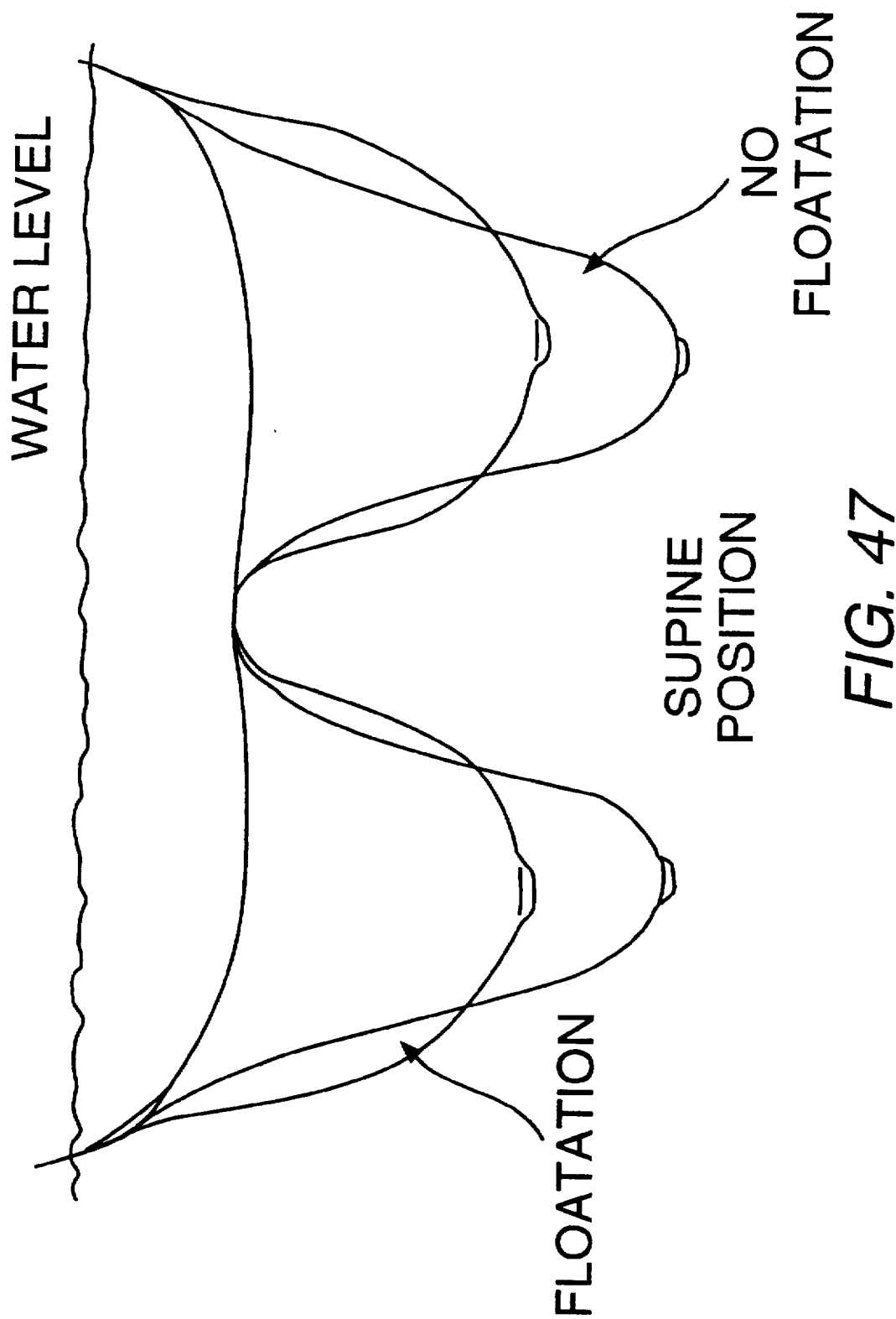
FIG. 47 compares the different shapes of the female breasts of a patient in a prone position with and without the levitating effects of floatation.

FIG. 47 compares the different shapes of the female breasts of a patient in a prone position with and without the levitating effects of floatation.

Figure 49:
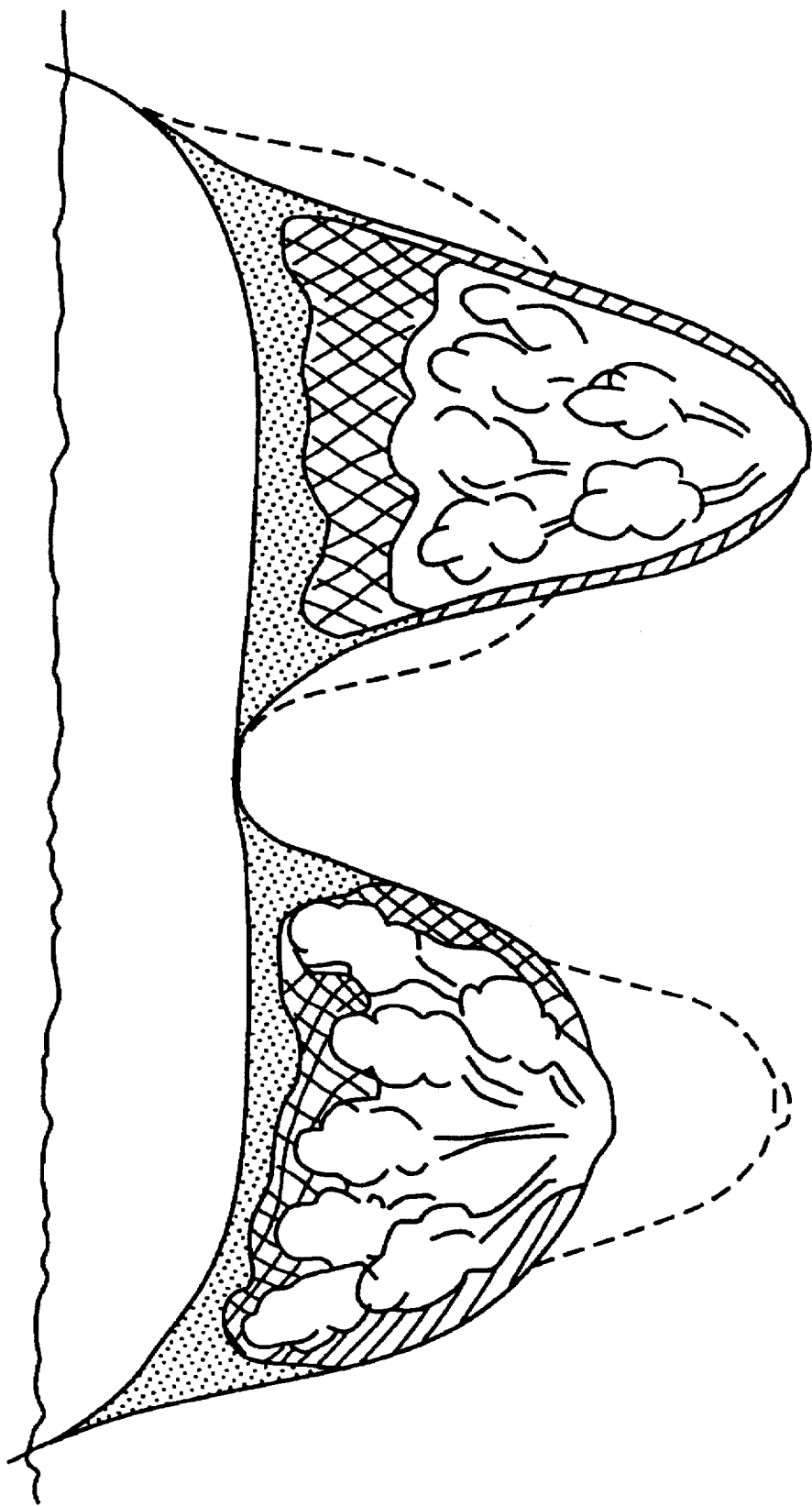

FIG. 48 reveals the migration of fatty tissue when a patient in a prone position immerses her breasts in water, while FIG. 49 portrays the emulsification of fatty tissue within the breast after immersion for twenty minutes. In FIG. 49, the non-emulsified areas are indicated by the darker shading. FIG. 50 illustrates the condition of the fatty tissue after submersion in a hot bath followed by cooling to room temperature.

FIG. 51 shows a breast in cross-section while the patient is in an upright position, and reveals the migration of fatty tissue. FIGS. 52 and 53 provide the same view as FIG. 51, but after a hot bath and massage.

FIG. 54 shows the fatty tissue migration into the internal structure of the breast when the patient is in a supine position. FIG. 55 shows the same breast after the emulsification that occurs during a hot bath and massage, while FIG. 56 illustrates the same tissue after it is cooled to normal body temperature.

Figure 57:
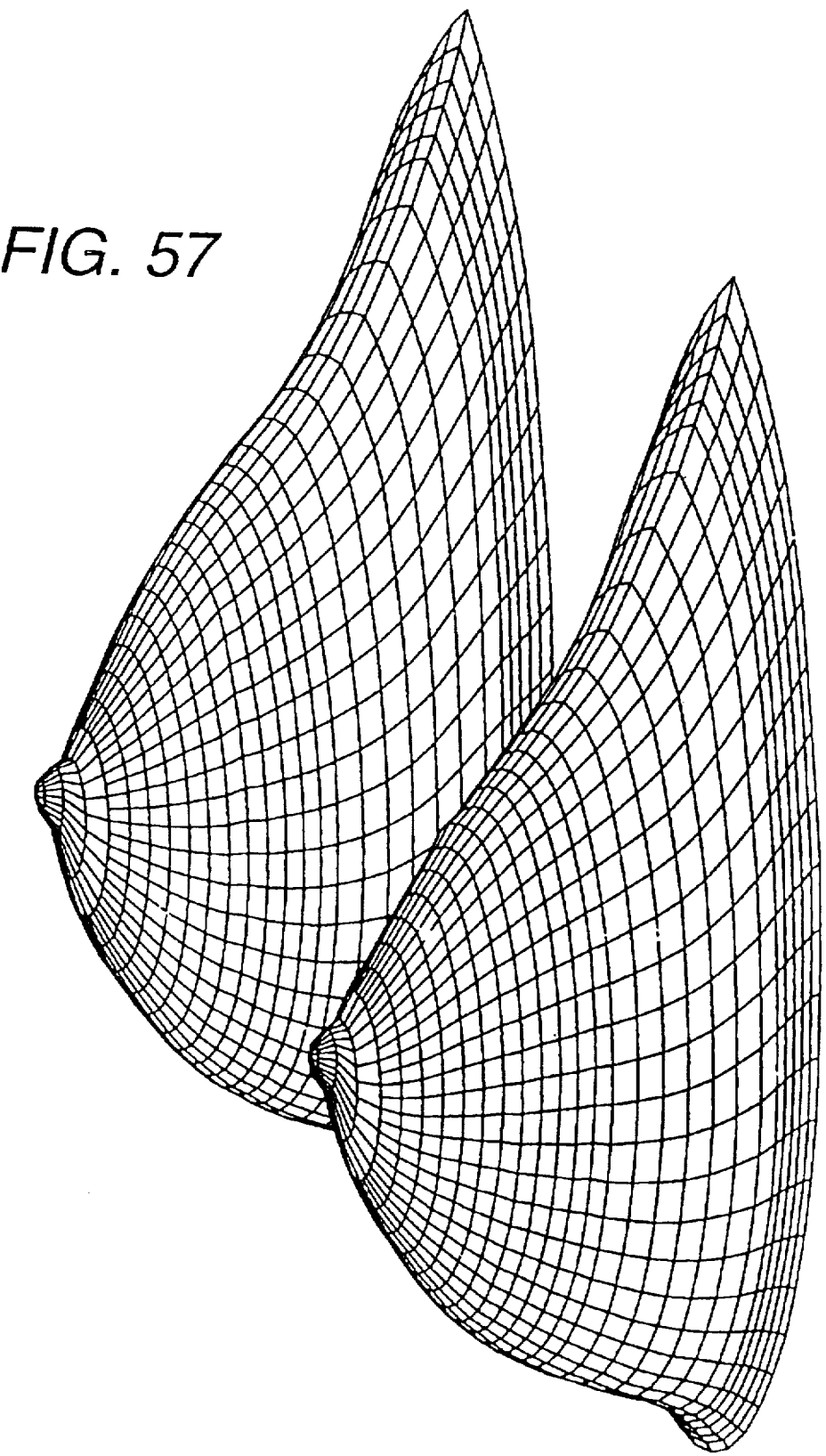
Figure 58:
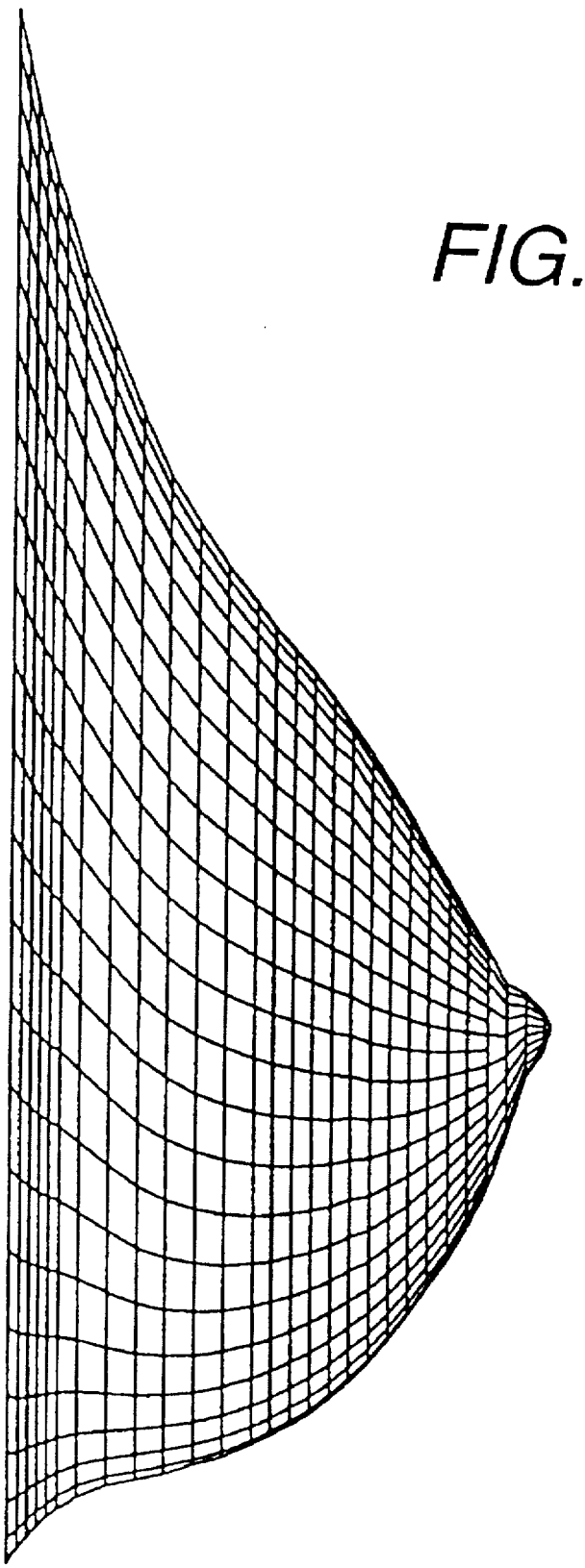
Figure 59:
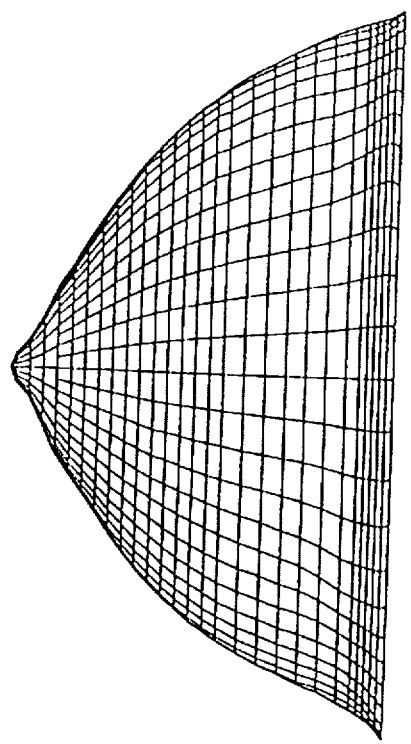
Figure 59:
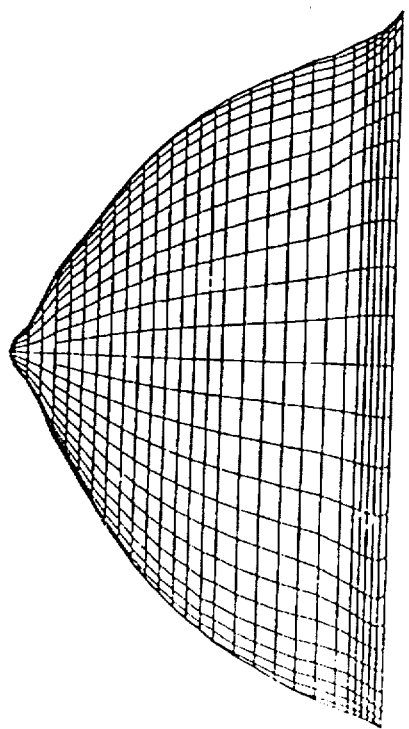
Figure 60:
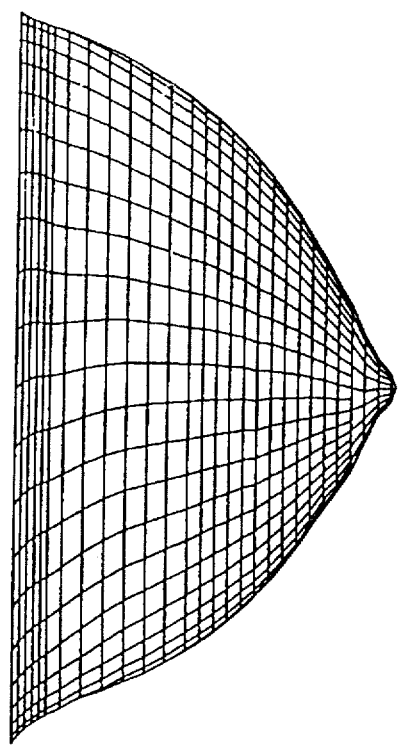
Figure 60:
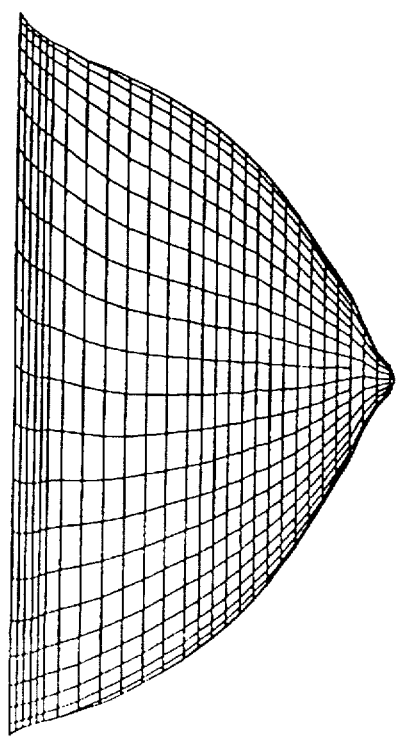
Figure 61:
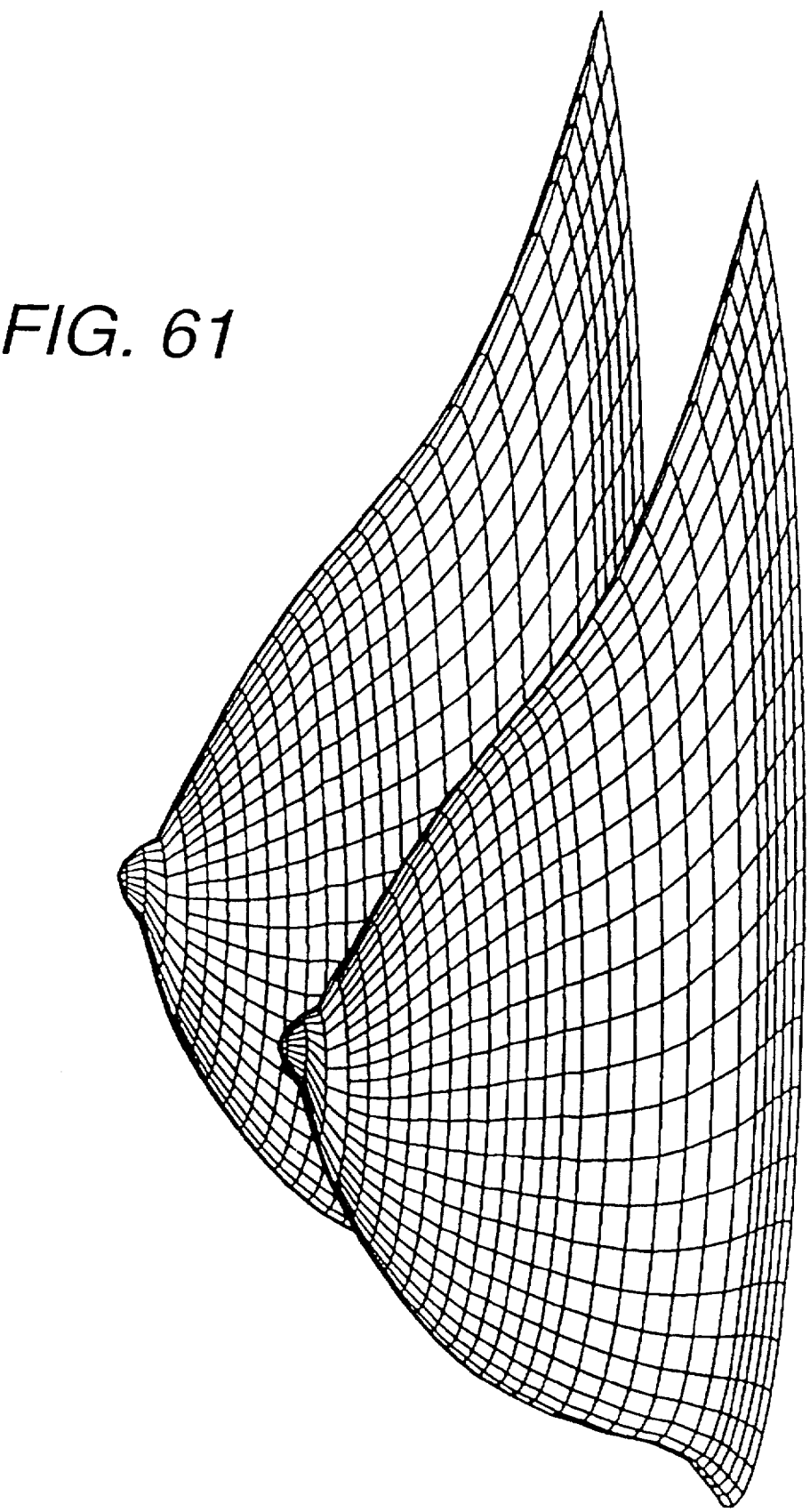
Figure 62:
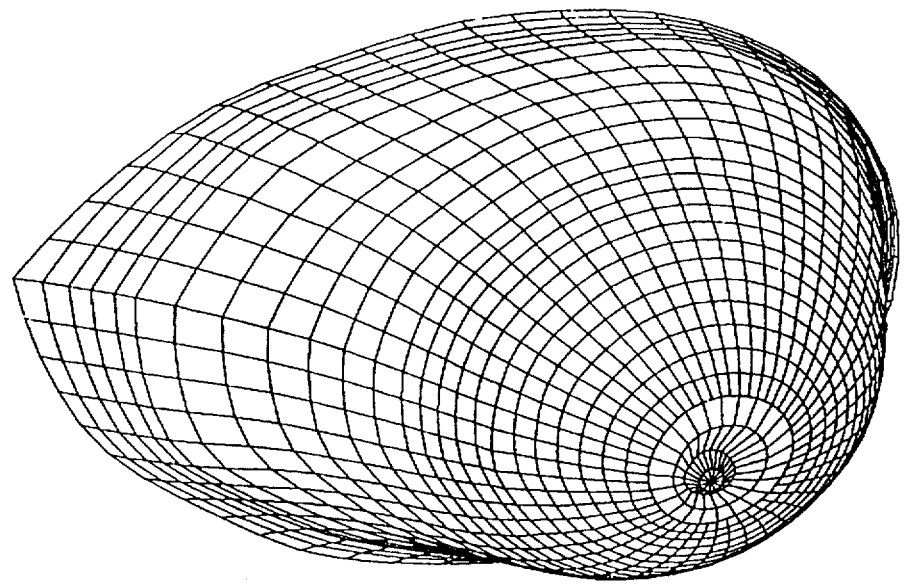
Figure 62:
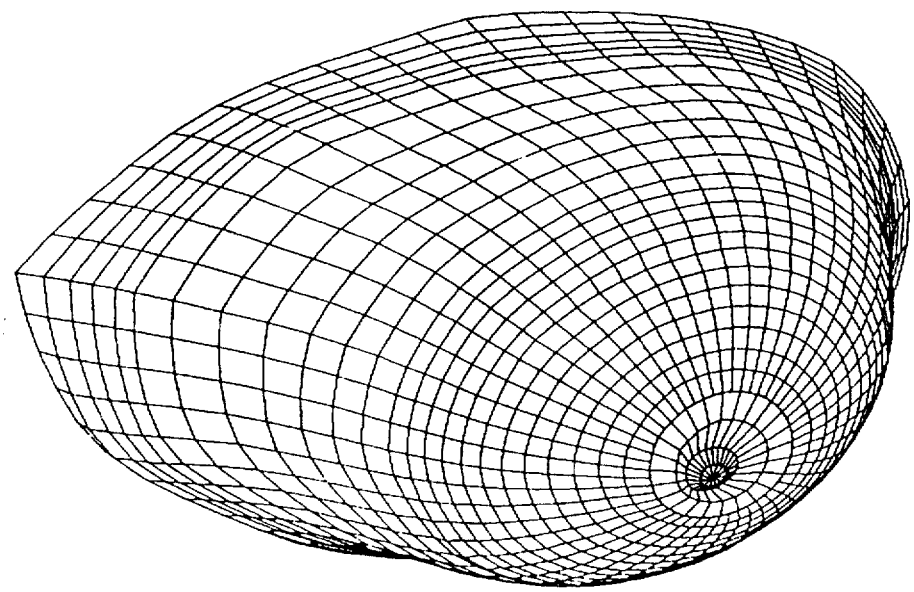
Figure 63:
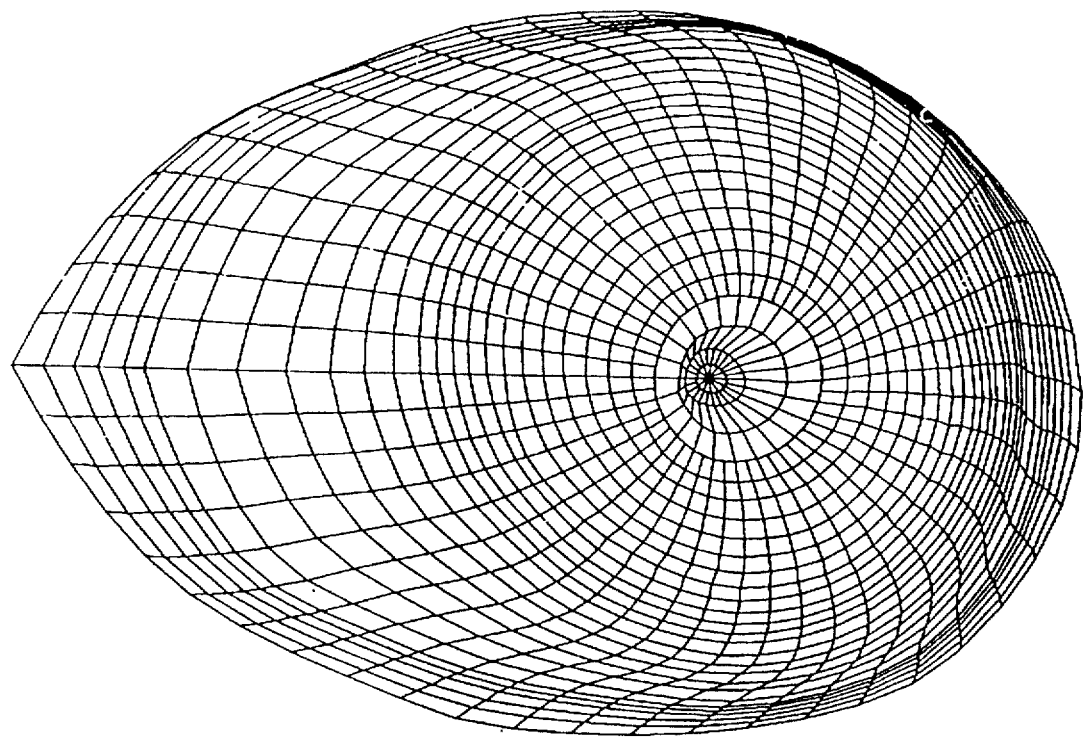
Figure 63:
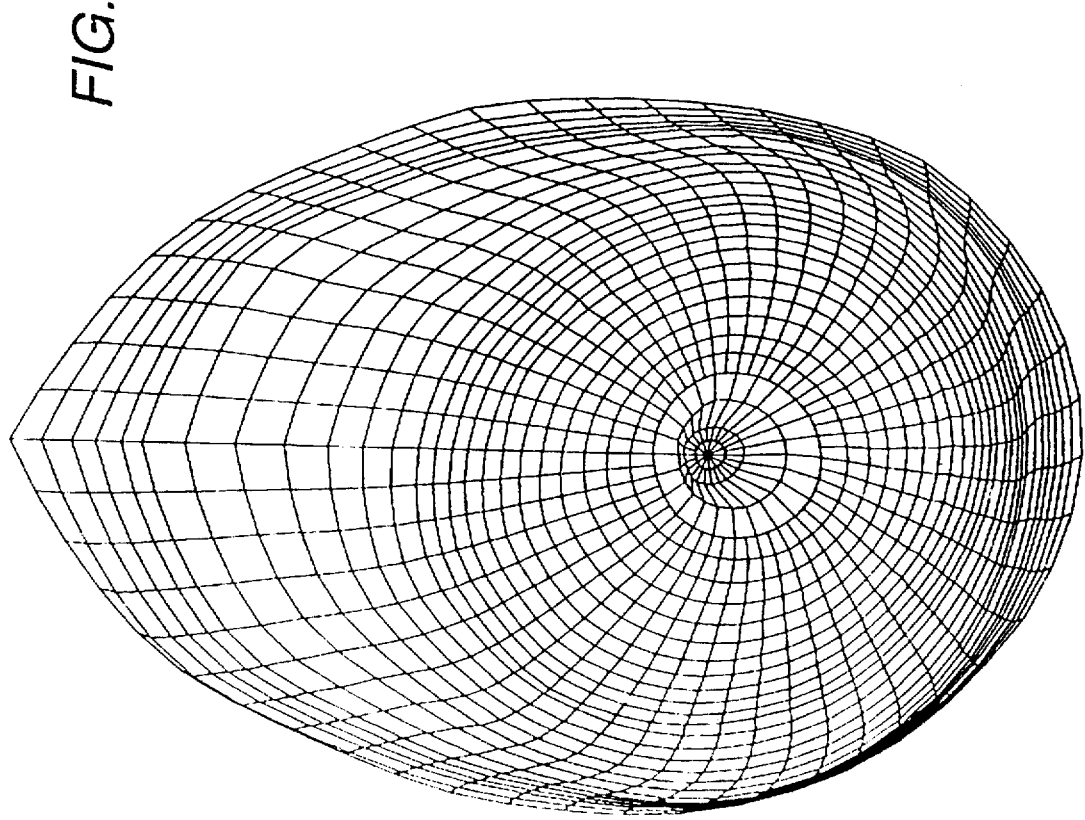
Figure 64:
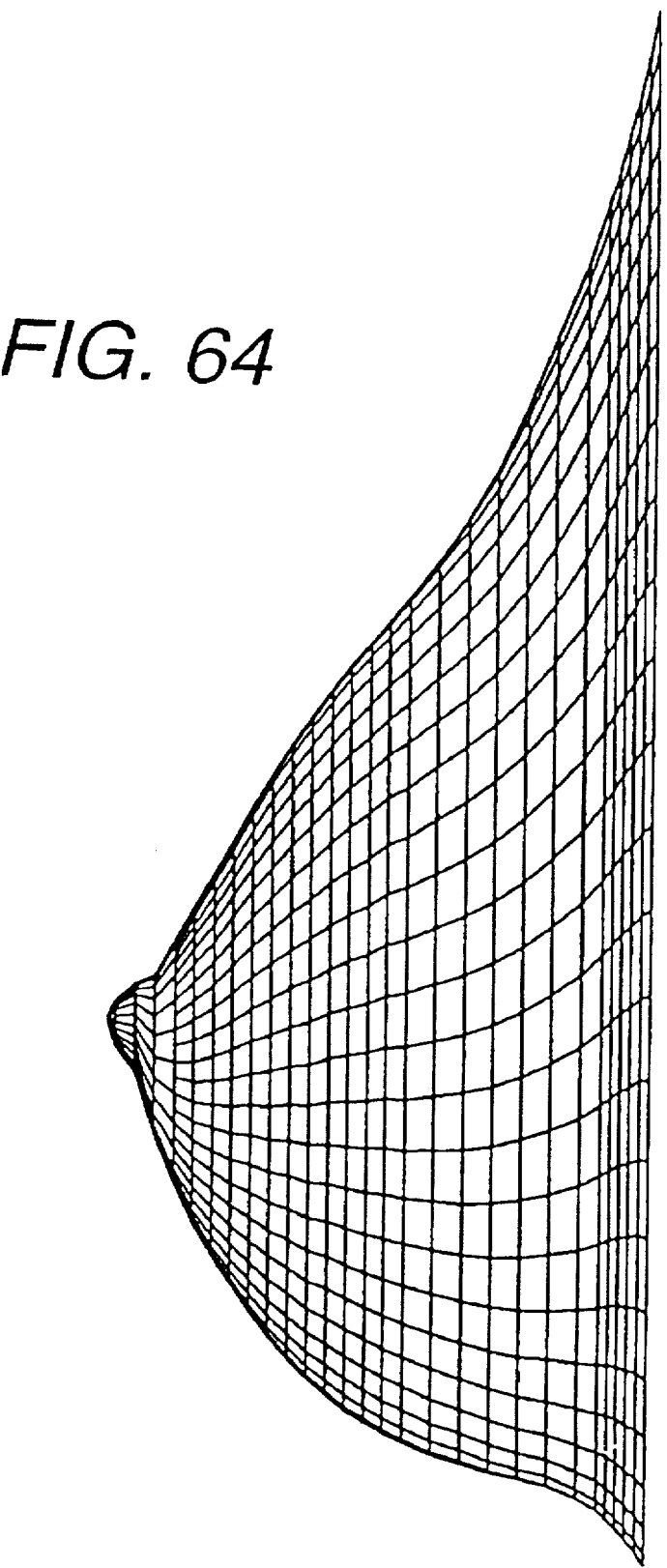

FIGS. 57 through 64 are computer-generated representations of breasts under floatation. FIG. 57 is a perspective view, FIG. 58 is a side view, FIG. 59 is a top view and FIG. 60 is a view taken from below the breasts. FIGS. 61, 62 and 63 offer additional perspective views, while FIG. 64 provides another side view. All of these computer-generated representations were created using a mold of a patient's breasts while they were under the influence of floatation. The mold was then measured by a three-dimensional sensor and mapped by computer software to produce the images found in FIGS. 57 through 64. These images may be used to manufacture clothing which is custom tailored to an individual's particular shape.

CONCLUSION

Although the present invention has been described in detail with reference to particular preferred and alternative embodiments, persons possessing ordinary skill in the art to which this invention pertains will appreciate that various modifications and enhancements may be made without departing from the spirit and scope of the Claims that follow. The imaging equipment that has been disclosed above is presented to educate the reader about particular embodiments, and is not intended to constrain the limits of the invention or the scope of the Claims. The List of Reference Characters which follows is intended to provide the reader with a convenient means of identifying elements of the invention in the Specification and Drawings. This list is not intended to delineate or narrow the scope of the Claims.

LIST OF REFERENCE CHARACTERS

10 Female breast in normal pendent position

12U Female breast immersed in water under influence of floatation in undeflected position 12D Deflected position of breast during examination 13 Constricted portion of breast 14 Internal structure of breast 16 Spa tub 17 Modular spa facility 18 Shower 20 Schematic block diagram of ultrasonic breast evaluation equipment and circuitry 22 Remote power source 24 Signal conditioner 26 Ultrasonic transducer 28 Signal processor 30 Control panel 32 Glove containing transducer 34 Finger cup F Finger FF Flat portion of finger FN Finger nail FT Finger tip RC Rib cage T Torso W Water WL Water level

What is claimed is:

1. A method of examining a portion of the body comprising the steps of:

immersing said portion of the body in a hot bath; and examining said portion of the body under the levitating and relaxing influence caused by the immersion of said portion of the body in said hot bath;

applying a probing pressure using the fingertips (FT);

using said probing pressure to form a relatively constricted three-dimensional projection of tissue; and palpating said portion of the body using the fingertips (FT) to detect abnormalities in said portion of the body.

2. A method as recited in claim 1, in which said portion of the body is a female breast.

3. A method as recited in claim 2, in which said hot bath partially emulsifies fatty tissue in said female breast which enhances the ability of said examiner to detect an abnormality.

4. A method as recited in claim 2, in which the levitating influence of said hot bath reduces the entanglement of the internal tissues of the breast which, in turn, enhances the ability of said examiner to detect an abnormality.

5. A method as recited in claim 2, in which said probing pressure is employed to examine the tissue overlying the lymph nodes in and around the pectoral muscles.

6. A method as recited in claim 2, in which said probing pressure is employed to examine the tissue around the arm pit.

7. A method as recited in claim 2, in which said probing pressure is employed to examine the tissue beneath the breast and overlying the rib cage.

8. A method as recited in claim 2, in which said probing pressure is employed to massage lumps residing in partially emulsified fatty tissues in said female breast.

9. A method as recited in claim 1, in which said portion of the body is a male testicle.

10. A method as recited in claim 1, in which said portion of the body is an abdomen.

11. A method as recited in claim 10, in which said abdomen is examined to detect a hernia.

12. A method as recited in claim 1, in which said hot bath utilizes water having a temperature in the range of approximately 101 to 104 degrees Fahrenheit.

13. A method as recited in claim 1, in which said fingertips are placed in generally opposing positions.

14. A method as recited in claim 1, in which said patient is in a generally upright position.

15. A method as recited in claim 1, in which said patient is in a generally upright position and is leaning forward slightly.

16. A method as recited in claim 1, in which said patient is leaning forward at an angle of approximately five to fifteen degrees.

17. A method as recited in claim 1, in which said patient is in a supine position.

18. A method as recited in claim 1, in which said patient is in a prone position.

19. A method as recited in claim 1, in which said patient is rotated approximately forty-five degrees from the supine position.

20. A method as recited in claim 1, in which said patient is rotated approximately forty-five degrees from the reclining position.

21. A method of examining a portion of a breast comprising the steps of:

immersing said portion of said breast in a hot bath; and examining said portion of said breast under the levitating influence caused by the immersion of said breast in said hot bath by applying a probing pressure using the fingertips (FT) of both hands; and palpating said breast by placing the finger tips (FT) in a generally opposed position generally near the rib cage and moving said fingertips out toward the nipple applying gentle pressure.

* * * * *